United States Patent
Grave et al.

(10) Patent No.: US 10,130,897 B2
(45) Date of Patent: Nov. 20, 2018

(54) CONTACTING A GAS STREAM WITH A LIQUID STREAM

(71) Applicants: Edward J. Grave, Montgomery, TX (US); John T. Cullinane, Montgomery, TX (US); Antonious J. A. M. Hendriks, Gelderland (NL); Tom Meekhof, Gelderland (NL); Frederik A. Lammers, Zoetermeer (NL)

(72) Inventors: Edward J. Grave, Montgomery, TX (US); John T. Cullinane, Montgomery, TX (US); Antonious J. A. M. Hendriks, Gelderland (NL); Tom Meekhof, Gelderland (NL); Frederik A. Lammers, Zoetermeer (NL)

(73) Assignee: ExxonMobil Upstream Research Company, Spring, TX (US)

(*) Notice: Subject to any disclaimer, the term of this patent is extended or adjusted under 35 U.S.C. 154(b) by 289 days.

(21) Appl. No.: 14/760,539

(22) PCT Filed: Oct. 24, 2013

(86) PCT No.: PCT/US2013/066686
§ 371 (c)(1),
(2) Date: Jul. 13, 2015

(87) PCT Pub. No.: WO2014/116310
PCT Pub. Date: Jul. 31, 2014

(65) Prior Publication Data
US 2015/0352463 A1 Dec. 10, 2015

Related U.S. Application Data

(60) Provisional application No. 61/739,674, filed on Jan. 25, 2013.

(51) Int. Cl.
*B01D 3/00* (2006.01)
*B01D 3/06* (2006.01)
(Continued)

(52) U.S. Cl.
CPC .............. *B01D 3/26* (2013.01); *B01D 3/008* (2013.01); *B01D 3/06* (2013.01); *B01D 53/1493* (2013.01);
(Continued)

(58) Field of Classification Search
CPC .......... B01D 2257/30; B01D 2257/304; B01D 2257/504; B01D 2257/80; B01D 53/14;
(Continued)

(56) References Cited

U.S. PATENT DOCUMENTS

| 1,951,647 A | 3/1934 | Cooke | 196/46 |
| 2,847,200 A | 8/1958 | Ung | 202/158 |

(Continued)

FOREIGN PATENT DOCUMENTS

| CA | 2144585 | 6/1996 | ............. B01D 53/52 |
| DE | 10162457 | 7/2003 | ............. B01D 3/32 |

(Continued)

OTHER PUBLICATIONS

U.S. Appl. No. 15/949,613, dated Apr. 10, 2018, Yeh, Norman K. et al.
(Continued)

*Primary Examiner* — Cabrena Holecek
(74) *Attorney, Agent, or Firm* — ExxonMobil Upstream Research Company Law Department

(57) ABSTRACT

A co-current contacting system is described herein. The co-current contacting system includes a co-current contactor located in-line within a pipe. The co-current contactor includes an annular support ring configured to maintain the co-current contactor within the pipe and a number of radial (Continued)

blades configured to allow a liquid stream to flow into the co-current contactor. The co-current contacts also includes a central gas entry cone configured to allow a gas stream to flow through a hollow section within the co-current contactor, wherein the co-current contactor provides for efficient incorporation of liquid droplets formed from the liquid stream into the gas stream. The co-current contacting system also includes a separation system configured to remove the liquid droplets from the gas stream.

27 Claims, 11 Drawing Sheets

(51) Int. Cl.
  B01D 3/26    (2006.01)
  B01D 53/14   (2006.01)
  B01D 53/18   (2006.01)
  C07C 7/11    (2006.01)
  C10L 3/10    (2006.01)
(52) U.S. Cl.
  CPC .............. *B01D 53/185* (2013.01); *C07C 7/11* (2013.01); *C10L 3/103* (2013.01); *C10L 3/104* (2013.01); *C10L 3/106* (2013.01); *B01D 53/1456* (2013.01); *B01D 2252/103* (2013.01); *C10L 2290/08* (2013.01); *C10L 2290/10* (2013.01); *C10L 2290/46* (2013.01); *C10L 2290/541* (2013.01)
(58) Field of Classification Search
  CPC ............ B01D 53/1406; B01D 53/1456; B01D 53/18; B01D 53/00; B01D 53/1425; B01D 53/1475; B01F 3/04021; B01F 5/0413; B01F 5/0471
  See application file for complete search history.

(56) References Cited

U.S. PATENT DOCUMENTS

| | | | |
|---|---|---|---|
| 3,767,766 A | 10/1973 | Tjoa et al. ................ 423/220 |
| 3,773,472 A | 11/1973 | Hausberg et al. ............ 422/169 |
| 3,989,811 A | 11/1976 | Hill ................................ 423/573 |
| 4,073,832 A * | 2/1978 | McGann ................ B01D 47/10 261/117 |
| 4,369,167 A | 1/1983 | Weir ........................... 423/210 |
| 4,421,725 A | 12/1983 | Dezael et al. ................ 423/228 |
| 4,603,035 A | 7/1986 | Connell et al. ............ 423/226 |
| 4,678,648 A | 7/1987 | Wynn ......................... 423/228 |
| 4,701,188 A | 10/1987 | Mims ............................... 55/20 |
| 4,752,307 A | 6/1988 | Asmus et al. ................... 55/73 |
| 4,824,645 A | 4/1989 | Kinsley .......................... 208/13 |
| 4,885,079 A | 12/1989 | Eppig et al. ..................... 208/13 |
| 5,067,971 A | 11/1991 | Bikson et al. ................... 55/16 |
| 5,085,839 A | 2/1992 | Scott et al. ................... 423/210 |
| 5,091,119 A | 2/1992 | Biddulph et al. ........... 261/114.3 |
| 5,093,094 A | 3/1992 | Van Kleek et al. ........... 423/224 |
| 5,186,836 A | 2/1993 | Gauthier et al. ............ 210/512.1 |
| 5,209,821 A | 5/1993 | Shaw et al. ................... 159/4.01 |
| 5,439,509 A | 8/1995 | Spink et al. .................... 95/166 |
| 5,462,584 A | 10/1995 | Gavlin et al. ................... 95/231 |
| 5,603,908 A | 2/1997 | Yoshida et al. .............. 423/220 |
| 5,648,053 A | 7/1997 | Mimura et al. .............. 423/210 |
| 5,664,426 A | 9/1997 | Lu ..................................... 62/93 |
| 5,713,985 A | 2/1998 | Hamilton ......................... 95/90 |
| 5,810,897 A * | 9/1998 | Konosu ................ B01D 47/06 55/418 |
| 5,837,105 A | 11/1998 | Stober et al. .................. 203/40 |
| 5,907,924 A | 6/1999 | Collin et al. .................... 45/194 |
| 5,988,283 A | 11/1999 | Gann ............................ 166/357 |
| 6,063,163 A | 5/2000 | Carmody ........................ 95/187 |
| 6,071,484 A | 6/2000 | Dingman et al. ............ 423/229 |
| 6,089,317 A | 7/2000 | Shaw ........................... 166/265 |
| 6,214,097 B1 | 4/2001 | Laslo ............................. 96/236 |
| 6,228,145 B1 | 5/2001 | Falk-Pedersen et al. ......... 95/44 |
| 6,830,608 B1 | 12/2004 | Peters ........................... 261/112 |
| 6,881,389 B2 | 4/2005 | Paulsen et al. ............... 423/210 |
| 7,018,451 B1 | 3/2006 | Torkildsen et al. ............. 95/216 |
| 7,128,276 B2 | 10/2006 | Nilsen et al. ................. 236/124 |
| 7,144,568 B2 | 12/2006 | Ricard et al. ................. 423/659 |
| 7,152,431 B2 | 12/2006 | Amin et al. ..................... 62/637 |
| 7,175,820 B2 | 2/2007 | Minkkinen et al. .......... 423/228 |
| RE39,826 E | 9/2007 | Lu ................................... 62/632 |
| 7,273,513 B2 | 9/2007 | Linga et al. .................... 95/235 |
| 7,811,343 B2 | 10/2010 | Toma ............................. 55/318 |
| 8,137,444 B2 | 3/2012 | Farsad et al. ................... 96/235 |
| 8,240,640 B2 | 8/2012 | Nakayama .................... 261/109 |
| 8,268,049 B2 | 9/2012 | Davydov ........................ 95/199 |
| 8,336,863 B2 | 12/2012 | Neumann et al. ............. 261/115 |
| 8,343,360 B2 | 1/2013 | Schook ......................... 210/788 |
| 8,475,555 B2 | 7/2013 | Betting et al. ................. 55/416 |
| 8,741,127 B2 | 6/2014 | Koseoglu et al. ................ 20/57 |
| 9,149,761 B2 | 10/2015 | Northrop et al. ............ 166/401 |
| 9,599,070 B2 | 3/2017 | Huntington et al. ............ 60/39 |
| 2001/0037876 A1 | 11/2001 | Oost et al. .................... 165/133 |
| 2003/0005823 A1 | 1/2003 | LeBlanc et al. ................ 95/149 |
| 2003/0155438 A1 | 8/2003 | Boee et al. ................. 239/533.2 |
| 2004/0092774 A1 | 5/2004 | Mimura et al. ............... 564/497 |
| 2005/0006086 A1 | 1/2005 | Gramme ..................... 166/105.5 |
| 2006/0123993 A1 | 6/2006 | Henriksen ...................... 96/234 |
| 2006/0185320 A1 | 8/2006 | Dureiko .......................... 52/749 |
| 2008/0006011 A1 | 1/2008 | Larnholm et al. .............. 55/421 |
| 2008/0107581 A1 | 5/2008 | Sparling et al. ............... 423/222 |
| 2008/0115532 A1 | 5/2008 | Jager ............................... 62/620 |
| 2008/0190291 A1 | 8/2008 | Krehbiel et al. ................ 95/241 |
| 2008/0257788 A1 | 10/2008 | Leito .............................. 209/44 |
| 2008/0290021 A1 | 11/2008 | Buijs et al. ................ 210/500.27 |
| 2009/0213687 A1 | 8/2009 | Linga et al. ................. 366/167.2 |
| 2009/0241778 A1 | 10/2009 | Lechnick et al. ............... 95/177 |
| 2011/0168019 A1 | 7/2011 | Northrop et al. ............... 95/186 |
| 2011/0185633 A1 | 8/2011 | Betting et al. ............... 48/127.5 |
| 2011/0217218 A1 | 9/2011 | Gupta .......................... 423/228 |
| 2011/0296869 A1 | 12/2011 | Buhrman et al. .............. 62/617 |
| 2012/0060691 A1 | 3/2012 | Bieri et al. ..................... 95/270 |
| 2012/0204599 A1 | 8/2012 | Northrop et al. .............. 62/617 |
| 2012/0238793 A1 | 9/2012 | Cullinane et al. ............. 585/833 |
| 2012/0240617 A1 | 9/2012 | Weiss et al. .................... 62/611 |
| 2013/0017144 A1 | 1/2013 | Menzel ......................... 423/542 |
| 2014/0033921 A1 | 2/2014 | Peck et al. ..................... 95/269 |
| 2014/0245889 A1 | 9/2014 | Hamre et al. .................. 95/223 |
| 2014/0331862 A1 | 11/2014 | Cullinane et al. .............. 95/186 |
| 2014/0335002 A1 | 11/2014 | Northrop et al. ............. 423/228 |
| 2014/0373714 A1 | 12/2014 | Cloud et al. ................... 95/273 |
| 2015/0013539 A1 | 1/2015 | Eriksen et al. ................. 95/172 |
| 2015/0083425 A1 | 3/2015 | Sullivan et al. |
| 2015/0135954 A1 | 5/2015 | Li et al. |
| 2015/0322580 A1 | 11/2015 | Little ............................ 205/554 |
| 2015/0352463 A1 | 12/2015 | Grave et al. .................... 95/219 |
| 2016/0199774 A1 | 7/2016 | Grave et al. .................... 95/235 |
| 2016/0236140 A1 | 8/2016 | Northrop et al. .............. 95/210 |
| 2016/0263516 A1 | 9/2016 | Freeman et al. .............. 423/226 |
| 2017/0157553 A1 | 6/2017 | Northrop et al. ............... 96/314 |
| 2017/0239612 A1 | 8/2017 | Mondkar et al. ............. 423/220 |
| 2018/0071674 A1 | 3/2018 | Freeman et al. .............. 423/228 |

FOREIGN PATENT DOCUMENTS

| | | | |
|---|---|---|---|
| EP | 0191985 | 8/1986 | ............ B01D 53/18 |
| EP | 0301623 | 2/1989 | ............ B01D 53/14 |
| EP | 1021237 | 3/1999 | ............ B01D 53/18 |
| EP | 1438484 | 4/2003 | ............ B01D 17/02 |
| EP | 1141520 | 5/2003 | ............ E21B 43/40 |
| EP | 1340536 | 9/2003 | ............ B01J 19/30 |
| GB | 1234862 | 6/1971 | ............ B01D 53/18 |
| WO | WO1993/010883 | 6/1993 | ............ B01D 53/14 |
| WO | WO1997/046304 | 12/1997 | ............ B01D 53/26 |
| WO | WO1999/013966 | 3/1999 | ............ B01D 53/18 |
| WO | WO2000/056844 | 9/2000 | ............ B01D 3/10 |
| WO | WO2002/032536 | 4/2002 | ............ B01D 17/00 |
| WO | WO2003/072226 | 9/2003 | ............ B01D 53/14 |
| WO | WO2004/070297 | 8/2004 | ................ F25J 3/06 |

(56) References Cited

FOREIGN PATENT DOCUMENTS

| WO | WO2009/140993 | 11/2009 | ............ B01D 45/16 |
| WO | WO2013/136310 | 9/2013 | ............ B01D 53/14 |
| WO | WO2014/094794 | 6/2014 | ............ B01D 17/04 |
| WO | WO2017/087056 | 5/2017 | ............ B01D 53/26 |

OTHER PUBLICATIONS

U.S. Appl. No. 15/950,867, dated Apr. 11, 2018, Ramkumar, Shwetha et al.

U.S. Appl. No. 15/964,866, dated Apr. 27, 2018, Yeh, Norman K. et al.

U.S. Appl. No. 62/548,171, dated Aug. 21, 2017, Denton, Robert D. et al.

U.S. Appl. No. 62/548,172, dated Aug. 21, 2017, Denton, Robert D. et al.

Carter, T. et al. (1998) "Addition of Static Mixers Increases Capacity in Central Texas Gas Plant," *Proc. of the 77th GPA Annual Conv.*, pp. 110-113.

Dow Chemical Company (Mar. 3, 2015) "Product Safety Assessment," *SELEXOL Solvents Product Brochure*, 3 pages.

Garrison, J. et al. (2002) "Keyspan Energy Canada Rimbey Acid Gas Enrichment with FLEXSORB SE PLUS Technology," *Proceedings 2002 Laurance Reid Gas Conditioning Conf., Norman, OK*, 8 pgs.

Hanna, James M. (2009) "Qatargas Expansion Projects: Why Change the Gas Treating Concept from Sulfinol-D?," OSGAT 2009 Proceedings 5th Int'l Conf., Mar. 31-Apr. 1, Abu Dhabi, UAE, 33 pgs.

Jones, S. G. et al. (2004) "Design, Cost & Operation of an Acid Gas Enrichment & Injection Facility," *Proceedings 2004 Laurance Reid Gas Conditioning Conf., Norman, OK*, 43 pgs.

Linga, H. et al. (2001) "New Selective $H_2S$ Removal Process for the Refining Industry," *Nat'l Petrochemical & Refiners Assoc.*, AM-01-35, 9 pgs.

Linga, H. et al. (2006) "Potentials and Applications for the Pro-Pure Co-Current Contactors," *13th Annual India Oil & Gas Rev. Symp., Mumbai, India*, 24 pgs.

Nilsen, F. et al. (2001) "Selective $H_2S$ Removal in 50 Milliseconds," *Gas Processors Assoc., Europe Annual Conference*, 12 pgs.

Nilsen, F. et al. (2002) "Novel Contacting Technology Selectively Removes $H_2S$," *Oil & Gas Journal.*, 17 pgs.

Nilsen, F. et al. (2002) "Selective $H_2S$ Removal Applications using Novel Contacting Technology," *Gas Processors Assoc.*, 13 pgs.

Nova Molecular Technologies, Inc. (Jul. 17, 2008) "Product Brochure," *FLEXSORB SE*, 1 page.

ProSep, Inc. (2007) "Selective $H_2S$-Removal with Amines (ProCap)," *Product Brochure*, 32 pgs.

ProSep, Inc. (2014) "ProDry," *Gas Portfolio Product Brochure*, 1 pg.

ProSep, Inc. (2014) "ProScav," *Gas Portfolio Product Brochure*, 1 pg.

Royan, T. et al. (1992) "Acid Gas Enrichment using FLEXSORB," *Proceedings 1992 Laurance Reid Gas Conditioning Conf., Norman, OK*, Mar. 2-4, 17 pgs.

Schutte & Koerting (2012) "Gas Scrubbers," *Product Brochure*, 14 pgs.

Smith, W. B. (2010) "Typical Amine and Glycol Treating Unit Compared to Gas Membrane Separation System for Wellhead $CO_2$ Trimming," *Laurance Reid Gas Conditioning Conf., Norman, OK*, Feb. 21-24, 2010, pp. 417-436.

True, Warran R. (1994) "New Mobile Bay Complex Exploits Major Sour Gas Reserve," *Oil & Gas Journal*, v. 92, No. 21, 4 pgs.

Weiland, R. H. (2008) "Acid Gas Enrichment—Maximizing Selectivity," *Proceedings 2008 Laurance Reid Gas Conditioning Conf., Clarita, OK*, 16 pgs.

\* cited by examiner

800

800

180,897 B2

CONTACTING A GAS STREAM WITH A LIQUID STREAM

CROSS-REFERENCE TO RELATED APPLICATION

This application is the National Stage of International Application No. PCT/US2013/066686, filed Oct. 24, 2013, which claims the priority benefit of U.S. Provisional Patent Application No. 61/739,674 filed Jan. 25, 2013 entitled CONTACTING A GAS STREAM WITH A LIQUID STREAM, the entirety of which is incorporated by reference herein.

FIELD OF INVENTION

The present techniques provide for the contacting of a gas stream with a liquid stream. More specifically, the present techniques provide for the incorporation of liquid droplets formed from a liquid stream into a gas stream using a co-current contactor.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

The production of hydrocarbons from a reservoir oftentimes carries with it the incidental production of non-hydrocarbon gases. Such gases include contaminants such as hydrogen sulfide ($H_2S$) and carbon dioxide ($CO_2$). When $H_2S$ or $CO_2$ are produced as part of a hydrocarbon gas stream, such as methane or ethane, the raw gas stream is sometimes referred to as "sour gas." The $H_2S$ and $CO_2$ are often referred to together as "acid gases."

In addition to hydrocarbon production streams, acid gases may be associated with synthesis gas streams, or with refinery gas streams. Acid gases may also be present within so-called flash-gas streams in gas processing facilities. Further, acid gases may be generated by the combustion of coal, natural gas, or other carbonaceous fuels.

Natural gas streams may contain not only $H_2S$ or $CO_2$, but may also contain other "acidic" impurities. These include mercaptans and other trace sulfur compounds ($SO_x$). In addition, natural gas streams may contain water. Such impurities are often removed prior to industrial or residential use.

Processes have been devised to remove contaminants from a raw natural gas stream. In the case of acid gases, cryogenic gas processing is sometimes used, particularly to remove $CO_2$ to prevent line freezing and plugged orifices. In other instances, particularly with $H_2S$ removal, the hydrocarbon fluid stream is treated with a solvent. Solvents may include chemical solvents such as amines. Examples of amines used in sour gas treatment include monoethanol amine (MEA), diethanol amine (DEA), and methyl diethanol amine (MDEA).

Physical solvents are sometimes used in lieu of amine solvents. Examples include Selexol® and Rectisol™. In some instances, hybrid solvents, meaning mixtures of physical and chemical solvents, have been used. An example is Sulfinol®. In addition, the use of amine-based acid gas removal solvents is very common.

Amine-based solvents rely on a chemical reaction with the acid gases. The reaction process is sometimes referred to as "gas sweetening." Such chemical reactions are generally more effective than the physical-based solvents, particularly at feed gas pressures below about 300 psia (2.07 MPa). There are instances where special chemical solvents such as Flexsorb™ are used, particularly for selectively removing $H_2S$ from $CO_2$-containing gas streams.

As a result of the gas sweetening process, a treated or "sweetened" gas stream is created. The sweetened gas stream is substantially depleted of $H_2S$ and/or $CO_2$ components. The sweetened gas stream can be further processed for liquids recovery, that is, by condensing out heavier hydrocarbon gases. The sweetened gas stream may be sold into a pipeline or may be used for liquefied natural gas (LNG) feed if the $CO_2$ concentration is less than, for example, about 50 ppm. In addition, the sweetened gas stream may be used as feedstock for a gas-to-liquids process, and then ultimately used to make waxes, butanes, lubricants, glycols, or other petroleum-based products. The extracted $CO_2$ may be sold, or it may be injected into a subterranean reservoir for enhanced oil recovery (EOR) operations.

When a natural gas stream contains water, a dehydration process is usually undertaken before acid gas removal. This is done through the use of glycol or other desiccant in a water separator. The dehydration of natural gas is performed to control the formation of gas hydrates and to prevent corrosion in distribution pipelines. The formation of gas hydrates and corrosion in pipelines can cause a decrease in flow volume as well as frozen control valves, plugged orifices, and other operating problems.

Traditionally, the removal of acid gases or water using chemical solvents or desiccants involves counter-currently contacting the raw natural gas stream with the chemical. The raw gas stream is introduced into the bottom section of a contacting tower. At the same time, the solvent solution is directed into a top section of the tower. The tower has trays, packing, or other "internals." As the liquid solvent cascades through the internals, it absorbs the undesirable components, carrying them away through the bottom of the contacting tower as part of a "rich" solvent solution. At the same time, gaseous fluid that is largely depleted of the undesirable components exits at the top of the tower.

The rich solvent or rich glycol that exits the contactor is sometimes referred to as an absorbent liquid. Following absorption, a process of regeneration (also called "desorption") may be employed to separate contaminants from the active solvent of the absorbent liquid. This produces a "lean" solvent or a "lean" glycol that is then typically recycled into the contacting tower for further absorption.

Known counter-current contactors used for dehydration or for $H_2S$ and $CO_2$ absorption tend to be very large and heavy. This creates particular difficulty in offshore oil and gas production applications where smaller equipment is desirable. Further, the transport and set-up of large tower-based facilities is difficult for shale gas production operations that frequently take place in remote locations.

SUMMARY

An exemplary embodiment provides a co-current contacting system. The co-current contacting system includes a co-current contactor located in-line within a pipe. The co-current contactor includes an annular support ring configured to maintain the co-current contactor within the pipe and a number of radial blades configured to allow a liquid stream to flow into the co-current contactor. The co-current contacts also includes a central gas entry cone configured to allow a gas stream to flow through a hollow section within the co-current contactor, wherein the co-current contactor provides for efficient incorporation of liquid droplets formed from the liquid stream into the gas stream. The co-current contacting system also includes a separation system configured to remove the liquid droplets from the gas stream.

Another exemplary embodiment provides a method for separating impurities from a gas stream. The method includes flowing a liquid stream into a co-current contactor via an annular support ring and a number of radial blades extending from the annular support ring, wherein the annular support ring secures the co-current contactor in-line within a pipe. The method also includes flowing a gas stream into the co-current contactor via a central gas entry cone that is supported by the radial blades, wherein a first portion of the gas stream flows through the central gas entry cone and a second portion of the gas stream flows around the central gas entry cone between the radial blades. The method further includes contacting the gas stream with the liquid stream to provide for incorporation of liquid droplets formed from the liquid stream into the gas stream and separating the liquid droplets from the gas stream within a separation system.

Another exemplary embodiment provides a co-current contactor. The co-current contactor includes an annular support ring configured to maintain the co-current contactor in-line within a pipe. The annular support ring includes a hollow channel configured to allow a liquid stream to flow into a number of radial blades extending from the annular support ring. The co-current contactor also includes a central gas entry cone configured to allow a gas stream to flow into the co-current contactor, wherein a first portion of the gas stream flows through the central gas entry cone and a second portion of the gas stream flows around the central gas entry cone between the radial blades. The co-current contactor is configured to provide for incorporation of liquid droplets formed from the liquid stream into the gas stream.

BRIEF DESCRIPTION OF THE DRAWINGS

The advantages of the present techniques are better understood by referring to the following detailed description and the attached drawings, in which.

DETAILED DESCRIPTION

Figure 1:
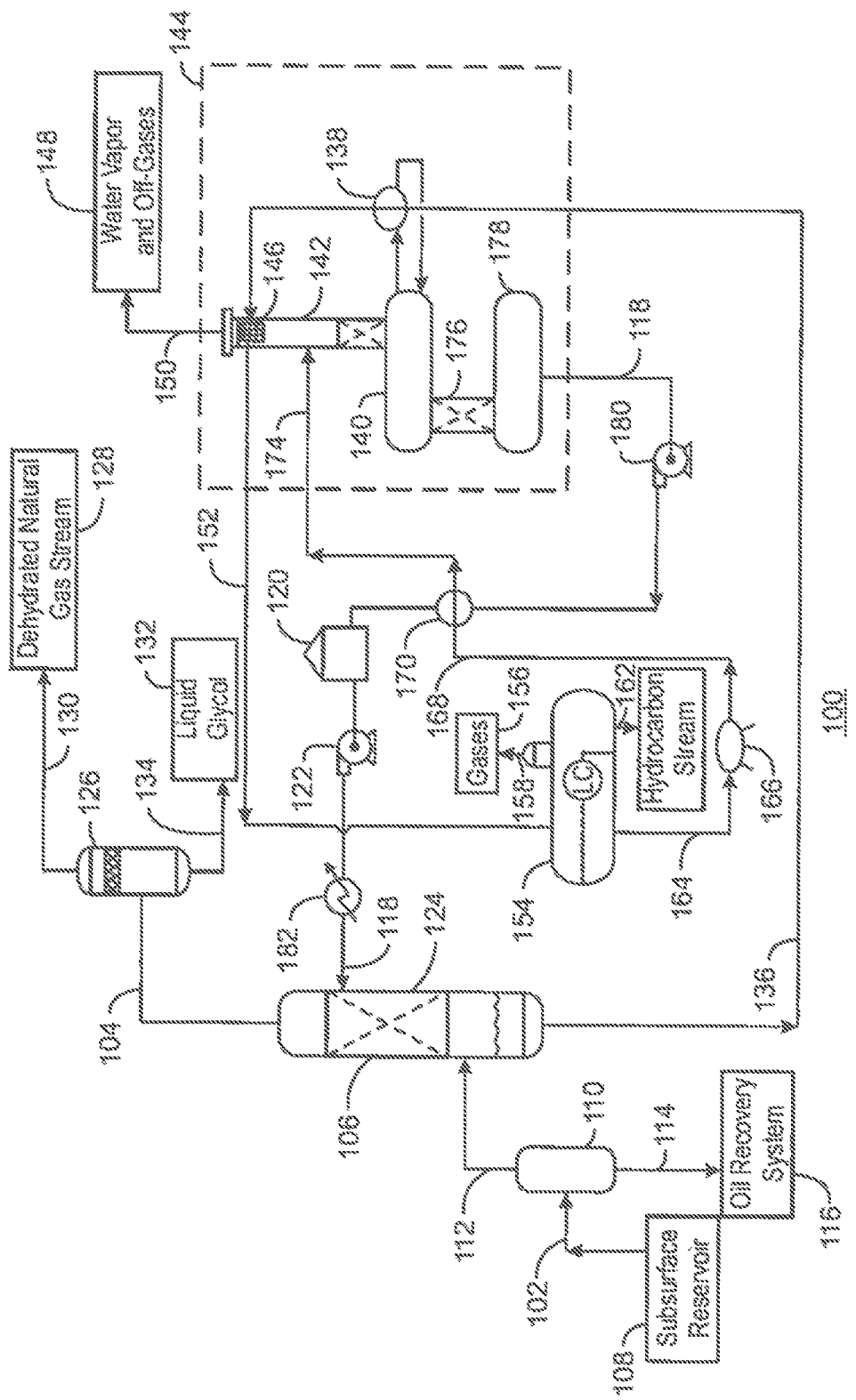
FIG. 1 is a process flow diagram of a chemical solvent-based gas processing facility.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

"Acid gas" refers to any gas that dissolves in water producing an acidic solution. Non-limiting examples of acid gases include hydrogen sulfide ($H_2S$), carbon dioxide ($CO_2$), sulfur dioxide ($SO_2$), carbon disulfide ($CS_2$), carbonyl sulfide (COS), mercaptans, or mixtures thereof.

"Co-current contacting device" or "co-current contactor" refers to a vessel that receives a stream of gas and a separate stream of solvent in such a manner that the gas stream and the solvent stream contact one another while flowing in generally the same directions within the contacting device. Non-limiting examples include an eductor and a coalescer, or a static mixer plus deliquidizer.

The term "co-currently" refers to the internal arrangement of process streams within a unit operation that can be divided into several sub-sections by which the process streams flow in the same direction.

As used herein, a "column" is a separation vessel in which a counter current flow is used to isolate materials on the basis of differing properties. In an absorbent column, a physical solvent is injected into the top, while a mixture of gases to be separated is flowed through the bottom. As the gases flow upwards through the falling stream of absorbent, one gas species is preferentially absorbed, lowering its concentration in the vapor stream exiting the top of the column. A portion of the overhead vapor may be condensed and pumped back into the top of the column as a reflux stream, which can be used to enhance the separation and purity of the overhead product. A bulk liquid stripper is related to a fractionation column. However, the bulk liquid stripper functions without the use of a reflux stream and, thus, cannot produce a high-purity overhead product.

In a distillation column, liquid and vapor phases are counter-currently contacted to effect separation of a fluid mixture based on boiling points or vapor pressure differences. The high vapor pressure, or lower boiling, component will tend to concentrate in the vapor phase whereas the low vapor pressure, or higher boiling, component will tend to concentrate in the liquid phase. Cryogenic separation is a separation process carried out in a column at least in part at temperatures at or below 150 degrees Kelvin (K). To enhance the separation, both types of columns may use a series of vertically spaced trays or plates mounted within the column and/or packing elements such as structured or random packing. Columns may often have a recirculated stream at the base to provide heat energy for boiling the fluids, called reboiling.

"Dehydrated gas feed stream" refers to a natural gas stream that has undergone a dehydration process. Typically the dehydrated gas feed stream has a water content of less than 50 ppm, and preferably less than 7 ppm. Any suitable process for dehydrating the natural gas stream can be used. Typical examples of suitable dehydration processes include, but are not limited to, treatment of the natural gas stream with molecular sieves or dehydration using glycol or methanol. Alternatively, the natural gas stream can be dehydrated by formation of methane hydrates; for example, using a dehydration process as described in WO 2004/070297.

As used herein, the term "dehydration" refers to the pre-treatment of a raw feed gas stream to partially or completely remove water and, optionally, some heavy hydrocarbons. This can be accomplished by means of a pre-cooling cycle, against an external cooling loop or a cold internal process stream, for example. Water may also be removed by means of pre-treatment with molecular sieves, e.g. zeolites, or silica gel or alumina oxide or other drying agents. Water may also be removed by means of washing with glycol, monoethylene gycol (MEG), diethylene gycol (DEG) or triethylene gycol (TEG), or glycerol. The amount of water in the gas feed stream is suitably less than 1 vol %, preferably less than 0.1 vol %, more preferably less than 0.01 vol %.

The term "distillation," or "fractionation," refers to the process of physically separating chemical components into a vapor phase and a liquid phase based on differences in the components' boiling points and vapor pressures at specified temperatures and pressures. Distillation is typically performed in a "distillation column," which includes a series of vertically spaced plates. A feed stream enters the distillation column at a mid-point, dividing the distillation column into two sections. The top section may be referred to as the rectification section, and the bottom section may be referred to as the stripping section. Condensation and vaporization occur on each plate, causing lower boiling point components to rise to the top of the distillation column and higher boiling point components to fall to the bottom. A re-boiler is located at the base of the distillation column to add thermal energy. The "bottoms" product is removed from the base of the distillation column. A condenser is located at the top of the distillation column to condense the product emanating from the top of the distillation column, which is called the distillate. A reflux pump is used to maintain flow in the rectification section of the distillation column by pumping a portion of the distillate back into the distillation column.

The term "enhanced oil recovery" (EOR) refers to processes for enhancing the recovery of hydrocarbons from subterranean reservoirs. Techniques for improving displacement efficiency or sweep efficiency may be used for the exploitation of an oil field by introducing displacing fluids or gas into injection wells to drive oil through the reservoir to producing wells.

As used herein, the term "fluid" refers to gases, liquids, and combinations of gases and liquids, as well as to combinations of gases and solids, and combinations of liquids and solids.

The term "flue gas" refers to any gas stream generated as a by-product of hydrocarbon combustion.

The term "gas" is used interchangeably with "vapor," and is defined as a substance or mixture of substances in the gaseous state as distinguished from the liquid or solid state. Likewise, the term "liquid" means a substance or mixture of substances in the liquid state as distinguished from the gas or solid state.

A "hydrocarbon" is an organic compound that primarily includes the elements hydrogen and carbon, although nitrogen, sulfur, oxygen, metals, or any number of other elements may be present in small amounts. As used herein, hydrocarbons generally refer to components found in natural gas, oil, or chemical processing facilities.

With respect to fluid processing equipment, the term "in series" means that two or more devices are placed along a flow line such that a fluid stream undergoing fluid separation moves from one item of equipment to the next while maintaining flow in a substantially constant downstream direction. Similarly, the term "in line" means that two or more components of a fluid mixing and separating device are connected sequentially or, more preferably, are integrated into a single tubular device.

The term "industrial plant" refers to any plant that generates a gas stream containing at least one hydrocarbon or an acid gas. One non-limiting example is a coal-powered electrical generation plant. Another example is a cement plant that emits $CO_2$ at low pressures.

"Liquefied natural gas" or "LNG" is natural gas generally known to include a high percentage of methane. However, LNG may also include trace amounts of other compounds. The other elements or compounds may include, but are not limited to, ethane, propane, butane, carbon dioxide, nitrogen, helium, hydrogen sulfide, or combinations thereof, that have been processed to remove one or more components (for instance, helium) or impurities (for instance, water and/or heavy hydrocarbons) and then condensed into a liquid at almost atmospheric pressure by cooling.

The term "liquid solvent" refers to a fluid in substantially liquid phase that preferentially absorbs one component over another. For example, a liquid solvent may preferentially absorb an acid gas, thereby removing or "scrubbing" at least a portion of the acid gas component from a gas stream or a water stream.

"Liquid-vapor contacting device" refers to a device that provides for the contacting and development of at least one interfacial surface between liquid and vapor in the device. Examples of liquid-vapor contacting devices include plate column, packed column, wetted-wall (falling film) column, spray chamber, heat exchanger, or any combination thereof. Examples of devices including plate columns and packed columns include distillation columns, fractionation columns, and stripping columns.

"Natural gas" refers to a multi-component gas obtained from a crude oil well or from a subterranean gas-bearing formation. The composition and pressure of natural gas can vary significantly. A typical natural gas stream contains methane ($CH_4$) as a major component, i.e., greater than 50 mol % of the natural gas stream is methane. The natural gas stream can also contain ethane ($C_2H_6$), higher molecular weight hydrocarbons (e.g., $C_3$-$C_{20}$ hydrocarbons), one or more acid gases (e.g., carbon dioxide or hydrogen sulfide), or any combinations thereof. The natural gas can also contain minor amounts of contaminants such as water, nitrogen, iron sulfide, wax, crude oil, or any combinations thereof. The natural gas stream may be substantially purified prior to use in embodiments, so as to remove compounds that may act as poisons.

"Non-absorbing gas" means a gas that is not significantly absorbed by a solvent during a gas treating or conditioning process.

"Solvent" refers to a substance capable at least in part of dissolving or dispersing one or more other substances, such as to provide or form a solution. The solvent may be polar, nonpolar, neutral, protic, aprotic, or the like. The solvent may include any suitable element, molecule, or compound, such as methanol, ethanol, propanol, glycols, ethers, ketones, other alcohols, amines, salt solutions, or the like. The solvent may include physical solvents, chemical solvents, or the like. The solvent may operate by any suitable mechanism, such as physical absorption, chemical absorption, chemisorption, physisorption, adsorption, pressure swing adsorption, temperature swing adsorption, or the like.

"Substantial" when used in reference to a quantity or amount of a material, or a specific characteristic thereof, refers to an amount that is sufficient to provide an effect that the material or characteristic was intended to provide. The exact degree of deviation allowable may depend, in some cases, on the specific context.

The term "sweetened gas stream" refers to a fluid stream in a substantially gaseous phase that has had at least a portion of acid gas components removed.

Overview

The present techniques provide for the contacting of a gas stream with a liquid stream. It will be understood that "gas stream" means substantially in the gas phase, but may contain entrained liquid and/or solid materials. Similarly, "liquid stream" means substantially in the liquid phase, but may contain entrained gas and/or solid materials.

More specifically, the present techniques provide for the incorporation of liquid droplets formed from a liquid stream into a gas stream using a co-current contactor. Such techniques may be used for a variety of applications. For example, such techniques are described herein with regard to the separation of impurities from a gas stream by allowing for the incorporation of the impurities from the gas stream into liquid droplets formed from the liquid stream using a co-current contactor. The co-current contactor is configured to contact the gas stream including the impurities with the liquid stream by injecting the liquid stream into the gas stream as a fine mist of droplets. The mist provides a high surface area for the incorporation of the impurities into the liquid stream, for example, by adsorption, dissolution, reaction, and the like. A purified gas stream may then be generated by separating the gas stream from the liquid stream including the incorporated impurities using a separation system. Further, according to embodiments described herein, a number of co-current contactors and a number of separation systems may be employed in series to progressively purify the gas stream.

Gas Processing System

FIG. 1 is a process flow diagram of a chemical solvent-based gas processing facility 100. The gas processing facility 100 may be used to remove water from a raw natural gas stream 102, generating a dehydrated natural gas stream 104. This may be accomplished by flowing the raw natural gas stream 102 into a contactor 106, which may remove the water from the raw natural gas stream 102. The dehydrated natural gas stream 104 may then be flowed out of the contactor 106 as an overhead stream. In addition, residual water and acid gas components may be removed in connection with a subsequent process, as discussed further herein.

The raw natural gas stream 102 may be obtained from a subsurface reservoir 108 via any suitable type of hydrocarbon recovery operation. The raw natural gas stream 102 may include a non-absorbing gas, such as methane. In addition, the raw natural gas stream 102 may include an acid gas, such as $H_2S$ or $CO_2$. For example, the raw natural gas stream 102 may include about 1 to about 10% $H_2S$ or about 1 to about 10% $CO_2$, along with the hydrocarbon gas.

As shown in FIG. 1, the raw natural gas stream 102 may be flowed into an inlet separator 110 upon entry into the gas processing facility 100. When entering the inlet separator 110, the raw natural gas stream 102 may be under a large amount of pressure. However, the pressure of the raw natural gas stream 102 may vary considerably, depending on the characteristics of the subsurface reservoir 108 from which the gas product is produced. For example, the pressure of the raw natural gas stream 102 may range between atmospheric pressure and several thousand psig. For natural gas treating applications, the pressure of the raw natural gas stream 102 may be boosted to about 100 psig, or about 500 psig, or greater, if desired.

The inlet separator 110 may clean the raw natural gas stream 102, for example, to prevent foaming of liquid solvent during a later acid gas treatment process. This may be accomplished by separating the raw natural gas stream into liquid-phase components and gas-phase components. The liquid-phase components may include heavy hydrocarbons, a small portion of water, and impurities such as brine and drilling fluids. Such components may be flowed out of the inlet separator 110 via a bottoms line 114, and may be sent to an oil recovery system 116. The gas-phase components may include natural gas and some amount of impurities, such as acid gases and water. Such components may be flowed out of the inlet separator 110 as the overhead natural gas stream 112.

From the inlet separator 110, the natural gas stream 112 may be flowed into the contactor 106. The contactor 106 may use a desiccant, such as a liquid glycol stream 118, to absorb water in the natural gas stream 112. The liquid glycol stream 118 may include various glycols, such as triethylene glycol, among others. The liquid glycol stream 118 may be stored in a glycol tank 120. A pump 122 may force the liquid glycol stream 118 from the glycol tank 120 into the contactor 106 under suitable pressure. For example, the pump 122 may boost the pressure of the liquid glycol stream 118 to about 1,000 psig or higher, depending on the pressure of the raw natural gas stream 102.

Once inside the contactor 106, gas within the natural gas stream 112 moves upward through the contactor 106. Typically, one or more trays 124 or other internals are provided within the contactor 106 to create indirect flow paths for the natural gas stream 112 and to create interfacial area between the gas and liquid phases. At the same time, the liquid from the liquid glycol stream 118 moves downward and across the succession of trays 124 in the contactor 106. The trays 124 aid in the interaction of the natural gas stream 112 with the liquid glycol stream 118.

The contactor 106 operates on the basis of a counter-current flow scheme. In other words, the natural gas stream 112 is directed through the contactor 106 in one direction, while the liquid glycol stream 118 is directed through the contactor 106 in the opposite direction. As the two fluid materials interact, the down-flowing liquid glycol stream 118 absorbs water from the up-flowing natural gas stream 112 to produce the dehydrated natural gas stream 104.

Upon exiting the contactor 106, the dehydrated natural gas stream 104 can be flowed through an outlet separator 126. The outlet separator 126, also referred to as a scrubber, may allow any liquid glycol carried over from the contactor 106 to fall out of the dehydrated natural gas stream 104. The outlet separator 126 may also be used as a water wash vessel to capture vapor-phase solvent. A final dehydrated natural gas stream 128 may be flowed out of the outlet separator 126 via an overhead line 130. Any residual liquid glycol 132 may drop out through a bottoms line 134.

A spent desiccant stream 136 flows from the bottom of the contactor 106. The spent desiccant stream 136 may be a glycol solution that is rich (e.g., enriched) in the absorbed water. The spent desiccant stream 136 may be at a relatively high temperature, such as about 90° to about 102° F., or higher. In various embodiments, the gas processing facility 100 includes equipment for regenerating the liquid glycol stream 118 from the spent desiccant stream 136, as discussed further herein.

From the contactor 106, the spent desiccant stream 136 may be flowed through a heat exchanger 138. Within the heat exchanger 138, the spent desiccant stream 136 may be cooled, providing heat to a reboiler 140 that is coupled to a distillation column 142 within a regenerator 144. The regenerator 144 may be used to regenerate the liquid glycol stream 118 from the spent desiccant stream 136. The regenerator 144 may be a large pressure vessel, or interconnect series of pressure vessels, that operates at about 15 to about 25 psig, for example.

The spent desiccant stream 136 can be flowed through a tube bundle 146 in the top of the distillation column 142. High-temperature water vapor and off-gases 148 being released from the distillation column 142 may preheat the spent desiccant stream 136 as it flows through the tube bundle 146, before the water vapor and off-gases 148 are released via an overhead line 150.

After being preheated within the distillation column 142, the spent desiccant stream 136 may be released from the tube bundle 146 as a warmed glycol stream 152. The warmed glycol stream 152 may be flowed into a flash drum 154. The flash drum 154 may operate at a pressure of about 50 to 100 psig, for example. The flash drum 154 may have internal parts that create a mixing effect or a tortuous flow path for the glycol stream 152.

Residual gases 156, such as methane, $H_2S$, or $CO_2$, may be flashed out of the flash drum 154 via an overhead line 158. The residual gases 156 captured in the overhead line 158 may be reduced to an acid gas content of about 100 ppm if contacted with an amine. This concentration of acid gases is small enough that the residual gases 156 can be used as fuel gas for the gas processing system 100.

In addition, any entrained heavier hydrocarbons, such as ethane or propane, within the glycol stream 152 may be captured within the flash drum 154. The resulting hydrocarbon stream may be flowed out of the flash drum 154 via a bottoms line 162.

Further, as the temperature and pressure of the glycol stream 152 drops within the flash drum 154, the hydrocarbons within the glycol stream 152 are separated out, producing a partially-purified glycol stream 164. The partially-purified glycol stream 164 may then be released from the flash drum 154. The partially-purified glycol stream 164 may be flowed through a filter 166, such as a carbon filter, for particle filtration.

The resulting filtered glycol stream 168 may then be flowed through a heat exchanger 170. Within the heat exchanger 170, the filtered glycol stream 168 may be heated via heat exchange with the liquid glycol stream 118. The resulting high-temperature glycol stream 174 may be flowed into the distillation column 142 of the regenerator 144. As the filtered glycol stream 168 travels through the distillation column 142, water vapor and off-gases 148, such as $H_2S$ and $CO_2$, may be removed from the filtered glycol stream 168.

The glycol stream 168 may be flowed out of the bottom of the distillation column 142 and into the reboiler 140. The reboiler 140 may increase the temperature of the glycol stream 168 using the heat generated by the heat exchanger 138. In addition, the reboiler 140 may boil off residual water vapor and off-gases 148 from the glycol stream 168. The components that are boiled off may travel upward through the distillation column 142 and become the water vapor and off-gases 148 in the overhead line 150.

The regenerator 144 may also include a separate stripping section 176 fed from the liquid pool in the reboiler 140. The stripping section 176 may include packing that promotes further distillation. Any remaining impurities, such as water, $H_2S$, or $CO_2$, boil off and join the water vapor and off-gases 148 in the overhead line 150. The glycol stream 174 may then be flowed into a surge tank 178, from which it may be released as the liquid glycol stream 118.

The regenerated liquid glycol stream 118 may be pumped out of the surge tank 178 via a pump 180. The pump 180 may increase the pressure of the liquid glycol stream 118 to about 1,500 psig or about 2,500 psig, for example.

The liquid glycol stream 118 is then flowed through the heat exchanger 170. Heat exchanged with the filtered glycol stream 168 in the heat exchanger 170 may serve to partially cool the liquid glycol stream 118. In addition, the liquid glycol stream 118 may be flowed through a cooler 182 prior to being returned to the contactor 106. The cooler 182 may cool the liquid glycol stream 118 to ensure that the liquid glycol stream 118 is not flashing when it is returned to the contactor 106. For example, the cooler 182 may chill the liquid glycol stream 118 to around 100° to 125° F.

The process flow diagram of FIG. 1 is not intended to indicate that the gas processing system 100 is to include all of the components shown in FIG. 1. Further, any number of additional components may be included within the gas processing system 100, depending on the details of the specific implementation. For example, the gas processing system 100 may include any suitable types of heaters, chillers, condensers, liquid pumps, gas compressors, blowers, bypass lines, other types of separation and/or fractionation equipment, valves, switches, controllers, and pressure-measuring devices, temperature-measuring devices, level-measuring devices, or flow-measuring devices, among others.

FIG. 1 demonstrates the use of a known contactor 106 in the context of a gas dehydration process. However, the gas processing facility 100 is also substantially representative of a sour gas removal operation. In that instance, the liquid glycol stream 118 includes a chemical solvent, such as a primary amine, a secondary amine, or a tertiary amine. The liquid glycol stream 118 may also be an ionic liquid or a blend of a physical solvent with an amine. For purposes of discussion, the liquid glycol stream 118 may be interchangeably referred to herein as an amine, a chemical solvent, or an absorbent liquid.

In some embodiments, a solvent that preferentially removes $H_2S$ molecules over $CO_2$ molecules may be used. For example, a tertiary amine typically does not effectively strip out $CO_2$ as quickly as $H_2S$. Therefore, two separate gas processing systems 100 may be sequentially operated, with one configured to strip out primarily $H_2S$, and the other configured to strip out primarily $CO_2$. A separate $CO_2$ stream that is substantially free of $H_2S$ may also be generated.

Regardless of the application and the solvent used, the disadvantage of gas processing systems that include counter-current flow schemes, such as the gas processing system 100 of FIG. 1, is that comparatively low velocities are required to avoid entrainment of the downflowing liquid solvent in the natural gas stream 102. Also, relatively long distances are required for disengagement of the liquid droplets from the natural gas stream 102. Depending on the flow rate of the natural gas stream 102, the contactor 106 can be greater than 15 feet in diameter, and more than 100 feet tall. For high-pressure applications, the vessel has thick, metal walls. Consequently, counter-current contactor vessels can be large and very heavy. This is expensive and undesirable, particularly for offshore oil and gas recovery applications.

In the gas processing system 100 of FIG. 1, the contactor 106 includes a single contacting tower. However, in some applications, more than one contacting tower may be used. In addition, very large contactors may be used for high-volume, high-pressure applications. In the case of low-pressure applications, such as $CO_2$ removal from flue gas at a power generation plant, it is estimated that a 50 foot by 50 foot duct contactor would be used for a relatively small, 500 megawatt power plant flue gas application. Many hundreds of gallons per minute of solvent would also be flowed through the contactor. Thus, such operations may become very costly.

Further, the internals of the tower 106 can make it susceptible to wave motion in an offshore environment. Therefore, it may be desirable to have a mass transfer process that does not rely on conventional tower internals. For example, utilize a series of low pressure-drop, small contacting devices to remove $CO_2$ or $H_2S$ from flash-gas streams.

Embodiments described herein utilize a co-current flow scheme as an alternative to the counter-current flow scheme demonstrated in the contactor 106 of FIG. 1. The co-current flow scheme utilizes one or more co-current contacting systems connected in series within a pipe. A natural gas stream and a liquid solvent may move together, i.e., co-currently, within the co-current contacting systems. In some embodiments, the natural gas stream and the liquid solvent move together generally along the longitudinal axis of the respective co-current contacting system. In general, co-current contactors can operate at much higher fluid velocities than counter-current contactors. As a result, co-current contactors tend to be smaller than counter-current contactors that utilize standard packed or trayed towers.

Figure 2A:
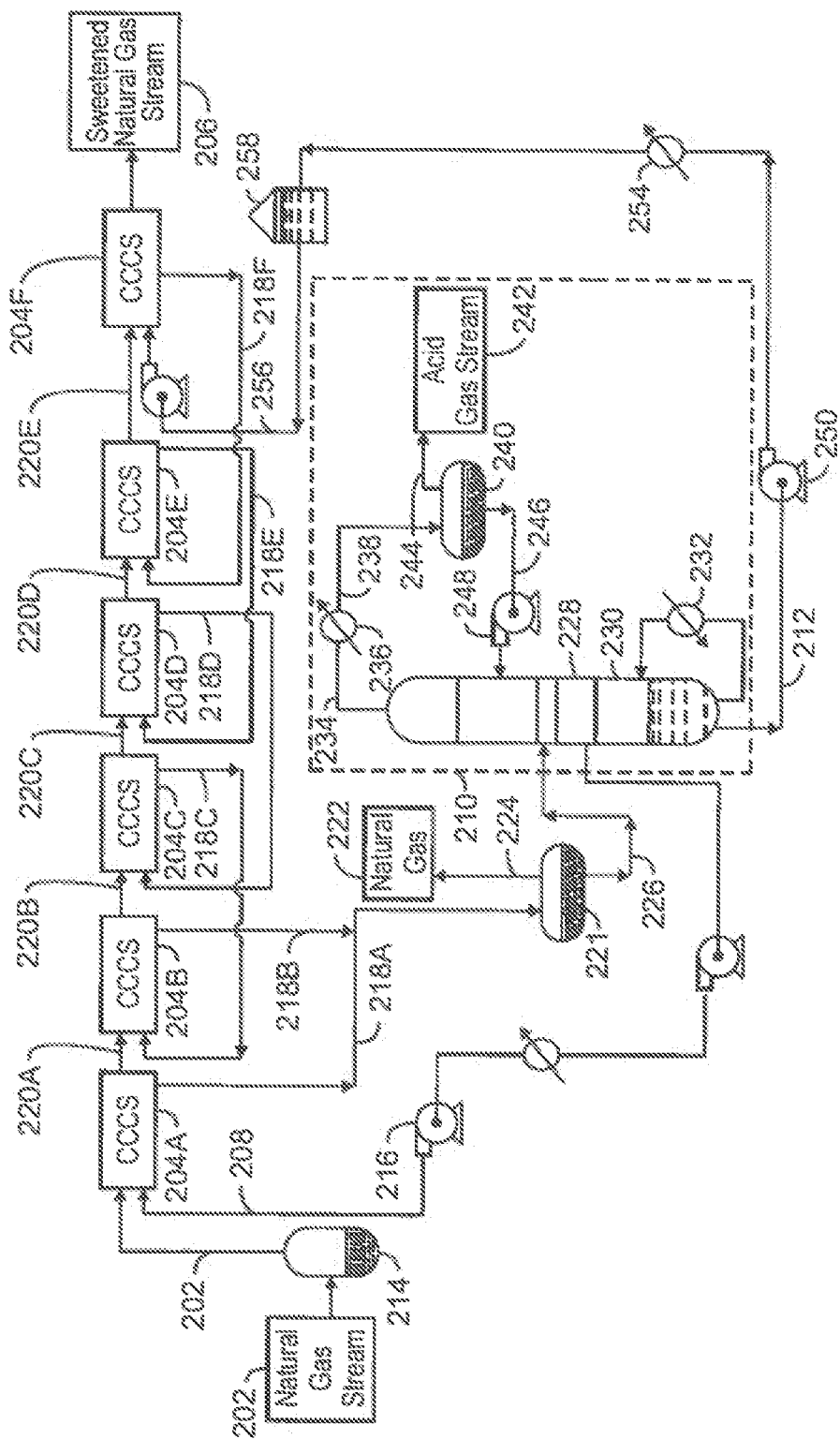
FIG. 2A is a process flow diagram of a gas processing system that includes a co-current flow scheme.

FIG. 2A is a process flow diagram of a gas processing system 200 that includes a co-current flow scheme. The gas processing system 200 may be an alternative to the gas processing system 100 discussed with respect to FIG. 1. The gas processing system 200 may be used for the removal of $H_2S$ or other acid gas components from a gas stream 202. In addition, in some embodiments, the gas processing system 200 may be used for the removal of water or other impurities from the gas stream 202. The gas processing system 200 may employ a number of co-current contacting systems 204A-F. Each co-current contacting system 204A-F may include a (one or more) co-current contactor(s) and/or separation system(s), for example, as discussed further with respect to FIG. 7.

The gas stream 202 may be a natural gas stream from a hydrocarbon production operation. For example, the gas stream 202 may be a flue gas stream from a power plant, or a synthesis gas (syn-gas) stream. If the natural gas stream 202 is a syn-gas stream, the gas stream 202 may be cooled and filtered before being introduced into the gas processing system 200. The gas stream 202 may also be a flash gas stream taken from a flash drum in a gas processing facility itself. In addition, the gas stream 202 may be a tail gas stream from a Claus sulfur recovery process or an impurities stream from a regenerator. Furthermore, the gas stream 202 may be an exhaust emission from a cement plant or other industrial plant. In this instance, $CO_2$ may be absorbed from excess air or from a nitrogen-containing flue gas.

The gas stream 202 may include a non-absorbing gas, such as methane, and one or more impurities, such as an acid gas. For example, the natural gas stream 202 may include $CO_2$ or $H_2S$. The gas processing system 200 may convert the gas stream 202 into a sweetened gas stream 206 by removing the acid gases.

In operation, the gas stream 202 may be flowed into a first co-current contacting system 204A, where it is mixed with a solvent stream 208. If the gas processing system 200 is to be used for the removal of $H_2S$, or other sulfur compounds, the solvent stream 208 may include an amine solution, such as monoethanol amine (MEA), diethanol amine (DEA), or methyldiethanol amine (MDEA). Other solvents, such as physical solvents, alkaline salts solutions, or ionic liquids, may also be used for $H_2S$ removal. In embodiments used for other purposes, such as dehydration or reactions, other solvents or reactants, such as glycols, may be used. The solvent stream 208 may include a lean solvent that has undergone a desorption process for the removal of acid gas impurities. For example, in the gas processing system 200 shown in FIG. 2A, the solvent stream 208 introduced into the first co-current contacting system 204A includes a semi-lean solvent that is taken from a central portion of a regenerator 210. A lean solvent stream 212 taken from the regenerator 210 may also be directed into a final co-current contacting system 204F.

In various embodiments, the gas processing system 200 employs a series of co-current contacting systems 204A-F. Each co-current contacting system 204A-F removes a portion of the acid gas content from the natural gas stream 202, thereby releasing a progressively sweetened natural gas stream in a downstream direction. The final co-current contacting system 204F provides the final sweetened natural gas stream 206.

Before entering the first co-current contacting system 204A, the natural gas stream 202 may pass through an inlet separator 214. The inlet separator 214 may be used to clean the natural gas stream 202 by filtering out impurities, such as brine and drilling fluids. Some particle filtration may also take place. The cleaning of the natural gas stream 202 can prevent foaming of solvent during the acid gas treatment process.

In some embodiments, the natural gas stream 202 may also be pretreated upstream of the inlet separator 214 or the first co-current contacting system 204A. For example, the natural gas stream 202 may undergo a water wash to remove glycol or other chemical additives. This may be accomplished via a separate processing loop (not shown) wherein water is introduced to the gas, such as via an additional co-current contacting system. Water has an affinity for glycol and will pull the glycol out of the natural gas stream 202. This, in turn, will help control foaming within the co-current contacting systems 204A-F. In the case of flue gas applications, corrosion inhibitors may be added to the solvent to retard the reaction of $O_2$ with the steel in the processes.

As shown in FIG. 2A, the solvent stream 208 is flowed into the first co-current contacting system 204A. Movement of the semi-lean solvent stream 208 into the first co-current contacting system 204A may be aided by a pump 216. The pump 216 may cause the semi-lean solvent stream 208 to flow into the first co-current contacting system 204A at a suitable pressure, for example, of about 15 psia to about 1,500 psig.

Once inside the first co-current contacting system 204A, the natural gas stream 202 and the solvent stream 208 move along the longitudinal axis of the first co-current contacting system 204A. As they travel, the liquid amine (or other treating solution) interacts with the $H_2S$, $H_2O$ (or other material) in the natural gas stream 202, causing the $H_2S$ to chemically attach to or be absorbed by the amine molecules. A first partially-loaded, or "rich," gas treating solution 218A may be flowed out of a bottom portion of the first co-current contacting system 204A. In addition, a first partially-sweetened natural gas stream 220A may be flowed out of a top portion of the first co-current contacting system 204A and into a second co-current contacting system 204B.

As shown in the example illustrated in FIG. 2A, a third co-current contacting system 204C may be provided after the second co-current contacting system 204B, and a fourth co-current contacting system 204D may be provided after the third co-current contacting system 204C. In addition, a fifth co-current contacting system 204E may be provided after the fourth co-current contacting system 204D, and a final co-current contacting system 204F may be provided after the fifth co-current contacting system 204E. Each of the second, third, fourth, and fifth co-current contacting systems 204B, 204C, 204D, and 204E may generate a respective partially-sweetened natural gas stream 220B, 220C, 220D, and 220E. In addition, each of the second, third, fourth, fifth, and final co-current contacting systems 204B, 204C, 204D, 204E, and 204F may generate respective partially-loaded gas treating solution 218B, 218C, 218D, 218E, and 218F. If an amine is used as the solvent stream 208, the partially-loaded gas treating solutions 218A-F may include rich amine solutions. In the gas processing system 200, the second loaded gas treating solution 218B merges with the rich gas treating solution 218A and goes through a regeneration process in the regenerator 210.

As the progressively-sweetened natural gas streams 220A-F are generated, the gas pressure in the gas processing system 200 will gradually decrease. As this occurs, the liquid pressure of the progressively-richer gas treating solutions 218A-F may be correspondingly increased. This may be accomplished by placing one or more booster pumps (not shown) between each co-current contacting system 204A-F to boost liquid pressure in the gas processing system 200.

In the gas processing system 200, solvent streams may be regenerated by flowing the partially-loaded gas treating solutions 218A and 218B through a flash drum 221. Absorbed natural gas 222 may be flashed from the partially-loaded gas treating solutions 218A and 218B within the flash drum 221, and may be flowed out of the flash drum 221 via an overhead line 224.

The resulting rich solvent stream 226 may be flowed from the flash drum 221 to the regenerator 210. The rich solvent stream 226 may be introduced into the regenerator 210 for desorption. The regenerator 210 may include a stripper portion 228 including trays or other internals (not shown). The stripper portion 228 may be located directly above a reboiler portion 230. A heat source 232 may be provided with the reboiler 230 to generate heat. The regenerator 210 produces the regenerated, lean solvent stream 212 that is recycled for re-use in the final co-current contacting system 204F. Stripped overhead gas from the regenerator 210, which may include concentrated $H_2S$ (or $CO_2$), may be flowed out of the regenerator 210 as an overhead impurities stream 234. The overhead impurities stream 234 may be flowed into a condenser 236, which may cool the overhead impurities stream 234. The resulting cooled impurities stream 238 may be flowed through a reflux accumulator 240. The reflux accumulator 240 may separate any remaining liquid, such as condensed water, from the impurities stream 238. This may result in the generation of a substantially pure acid gas stream 242, which may be flowed out of the reflux accumulator 240 via an overhead line 244.

In some embodiments, if the initial natural gas stream 202 includes $CO_2$, and a $CO_2$-selective solvent stream 208 is used, the acid gas stream 242 includes primarily $CO_2$. The $CO_2$-rich acid gas stream 242 may be used as part of a miscible EOR operation to recover oil. If the oil reservoir to be flooded does not contain a significant amount of $H_2S$ or other sulfur compounds, the $CO_2$ to be used for the EOR operation may not contain significant $H_2S$ or other sulfur compounds. However, concentrated $CO_2$ streams from oil and gas production operations may be contaminated with small amounts of $H_2S$. Thus, it may be desirable to remove the $H_2S$ from the $CO_2$, unless the acid gas stream 242 is to be injected purely for geologic sequestration.

In some embodiments, if the initial natural gas stream 202 includes $H_2S$, an $H_2S$-selective solvent stream 208 may be used to capture the $H_2S$. The $H_2S$ may then be converted into elemental sulfur using a sulfur recovery unit (not shown). The sulfur recovery unit may be a so-called Claus unit. Those of ordinary skill in the art will understand that a "Claus process" is a process that is sometimes used by the natural gas and refinery industries to recover elemental sulfur from $H_2S$-containing gas streams.

In practice, the "tail gas" from the Claus process, which may include $H_2S$, $SO_2$, $CO_2$, $N_2$ and water vapor, can be reacted to convert the $SO_2$ to $H_2S$ via hydrogenation. The hydrogenated tail gas stream has a high partial pressure, a large amount of $CO_2$, e.g., more than 50%, and a small amount of $H_2S$, e.g., a few percent or less. This type of gas stream, which is typically near atmospheric pressure, is amenable to selective $H_2S$ removal. The recovered $H_2S$ may be recycled to the front of the Claus unit, or may be sequestered downstream. Alternatively, a direct oxidation of the $H_2S$ to elemental sulfur may be performed using various processes known in the field of gas separation.

Because the $H_2S$ reaction is instantaneous relative to the $CO_2$ reactions, lowering the residence time, i.e., the contact time between the vapor and liquid phases, will result in less $CO_2$ being absorbed into the solvent. The design of the co-current contacting systems 204A-F enhances selective $H_2S$ removal due to the short contact time inherent in the equipment design.

As shown in FIG. 2A, a residual liquid stream 246 may be flowed out of the bottom of the reflux accumulator 240. The residual liquid stream 246 may be flowed through a reflux pump 248, which may boost the pressure of the residual liquid stream 246 and pump the residual liquid stream 246 into the regenerator 210. The residual liquid stream 246 may be flowed out of the regenerator 210, for example, from the bottom of the reboiler portion 230 as part of the lean solvent stream 212. Some water may be added to the lean solvent stream 212 to balance the loss of water vapor to the partially sweetened natural gas streams 220A-E. This water may be added at an intake or suction of the reflux pump 248.

The lean solvent stream 212 may be at a low pressure. Accordingly, the lean solvent stream 212 may be passed through a pressure boosting pump 250. From the pressure boosting pump 250, the lean solvent stream 212 may be flowed through a cooler 254. The cooler 254 may cool the lean solvent stream 212 to ensure that the lean solvent stream 212 will absorb acid gases effectively. The resulting chilled lean solvent stream 256 is then used as the solvent stream for the final co-current contacting system 204F.

In some embodiments, a solvent tank 258 is provided proximate the final co-current contacting system 204F. The chilled lean solvent stream 256 may be flowed from the solvent tank 258. In other embodiments, the solvent tank 258 is off-line and provides a reservoir for the lean solvent stream 256.

The process flow diagram of FIG. 2A is not intended to indicate that the gas processing system 200 is to include all of the components shown in FIG. 2A. Further, any number of additional components may be included within the gas processing system 200, depending on the details of the specific implementation. For example, the gas processing system 200 may include any suitable types of heaters, chillers, condensers, liquid pumps, gas compressors, blowers, bypass lines, other types of separation and/or fractionation equipment, valves, switches, controllers, and pressure-measuring devices, temperature-measuring devices, level-measuring devices, or flow-measuring devices, among others.

Figure 2B:
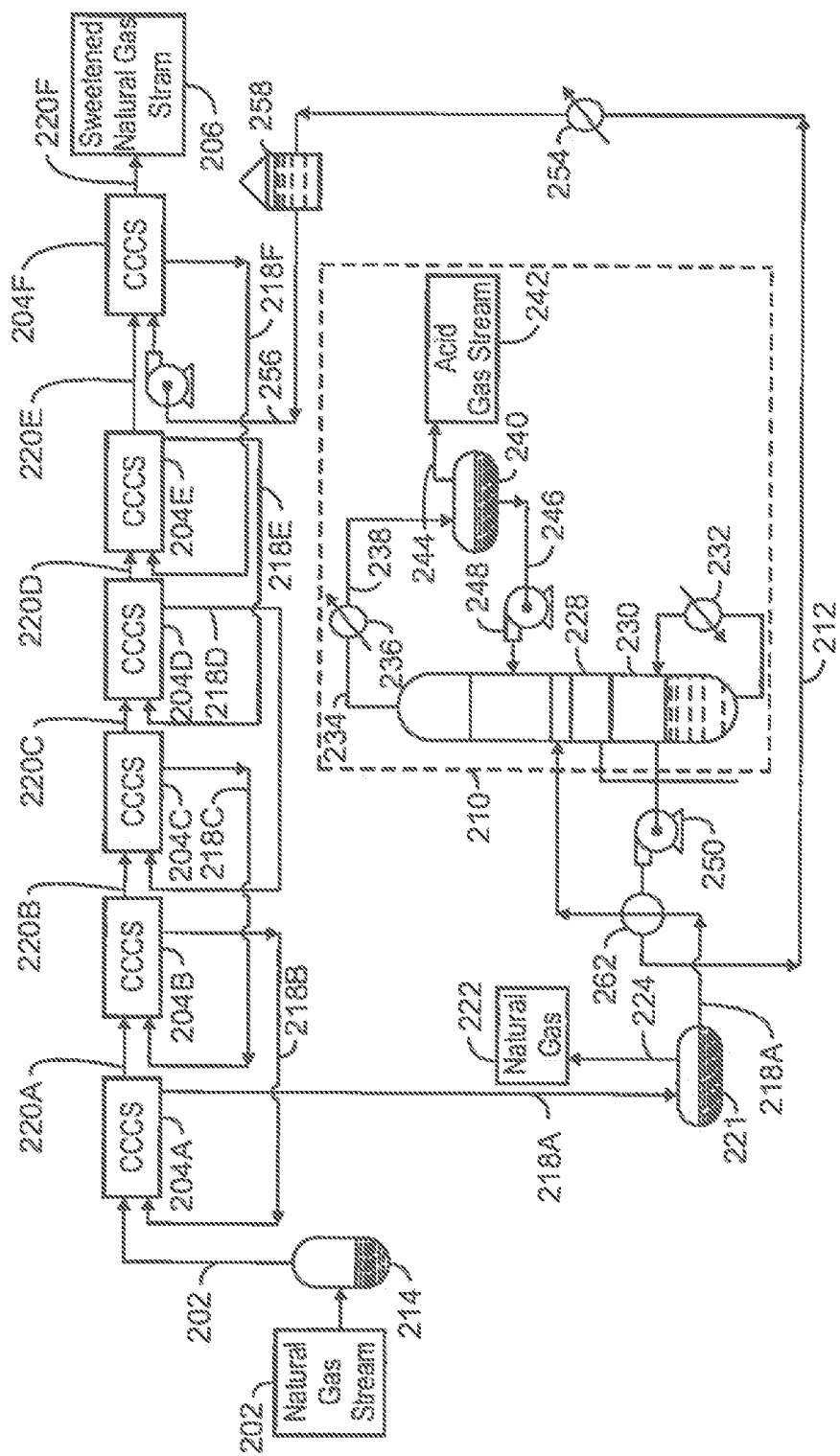
FIG. 2B is a process flow diagram of another gas processing system that includes a co-current flow scheme.

FIG. 2B is a process flow diagram of another gas processing system 260 that includes a co-current flow scheme. Like numbered items are as described with respect to FIG. 2A. Operation of the gas processing system 260 of FIG. 2B is similar to that of the gas processing system 200 of FIG. 2A. However, in the gas processing system 260, the first co-current contacting system 204A receives the partially-loaded gas treating solution 218B from the second co-current contacting system 204B. Therefore, the gas processing system 260 does not include the semi-lean solvent stream 208. In this example, the series of co-current contacting systems 204A-F acts like a separation column, for example, wherein each stage corresponds to a packed stage, as discussed with respect to FIG. 3.

Because the liquid solvent partially-loaded gas treating solution 218B received by the first co-current contacting system 204A in FIG. 2B has already been processed through the second co-current contacting system 204B, the partially-loaded gas treating solution 218B received by the first co-current contacting system 204A may be very rich. For this reason, it may be desirable to provide some level of intermediate processing of the partially-loaded gas treating solution 218B.

Alternatively, a semi-lean gas stream could be taken from other sweetening operations in the gas processing system 260 and used, at least in part, as an amine solution for the first or second co-current contacting system 204A or 204B. In this respect, there are situations in which a single type of solvent is used for more than one service in the gas processing system 260. This is referred to as integrated gas treatment. For example, MDEA may be used both for high-pressure, $H_2S$-selective acid gas removal, as well as in a Claus tail gas treating (TGT) process. The rich amine stream from the TGT process is not heavily loaded with $H_2S$ and $CO_2$, owing to the low pressure of the process. Thus, in some embodiments, the rich amine stream from the TGT process is used as a semi-lean stream for the first or second co-current contacting system 204A or 204B. The semi-lean stream (not shown) may be pumped to a suitable pressure and injected into the first or second co-current contacting system 204A or 204B, possibly along with the partially-loaded gas treating solution from the succeeding co-current contacting system.

Further, in the gas processing system 260 of FIG. 2B, the first partially-loaded solvent solution 218A is flowed through a heat exchanger 262 after being flowed through the flash drum 221. Within the heat exchanger 262, the temperature of the first partially-loaded solvent solution 218A is increased via heat exchange with the lean solvent 212 taken from the regenerator 210. This serves to heat the first partially-loaded solvent solution 218A before introduction into the regenerator 210, while cooling the lean solvent stream 212.

The process flow diagram of FIG. 2B is not intended to indicate that the gas processing system 260 is to include all of the components shown in FIG. 2B. Further, any number of additional components may be included within the gas processing system 260, depending on the details of the specific implementation.

Figure 3:
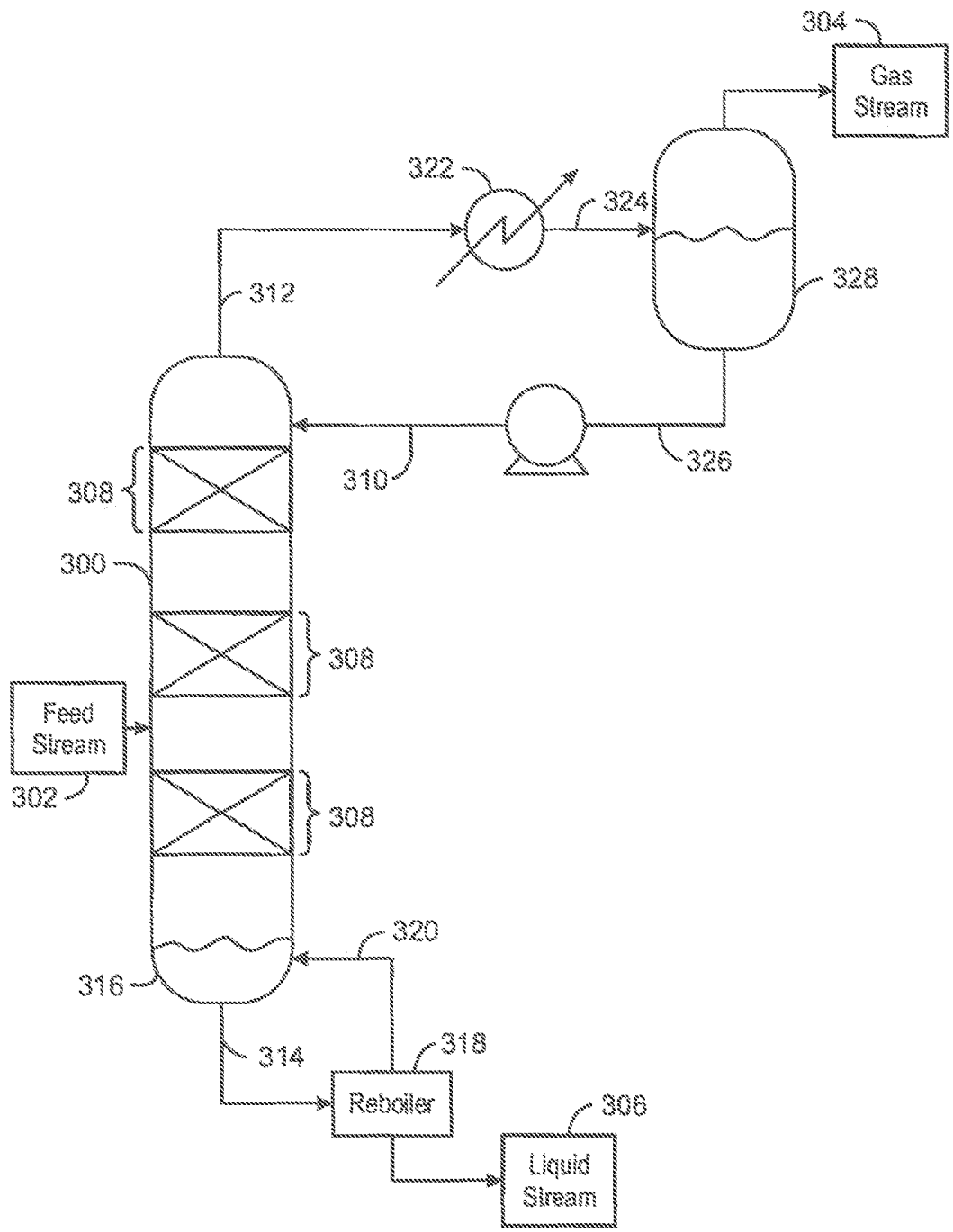
FIG. 3 is a schematic of a column for separating a feed stream into a gas stream and a liquid stream.

FIG. 3 is a schematic of a column 300 for separating a feed stream 302 into a gas stream 304 and a liquid stream 306. The feed stream 302 may be a gas stream that includes two or more different components with different boiling points and vapor pressures, such as an absorbent solvent and a gas contaminant. The column 300 may be similar to the columns used in the regenerators 144 and 210 discussed with respect to FIGS. 1, 2A, and 2B.

The column 300 may include a number of trays 308 or other internals that create indirect flow paths for the feed stream 302 and create interfacial area between the gas and liquid phases. The feed stream 302 may be injected into a lower or middle portion of the column 300, between trays 308. The gas within the feed stream 302 may move upward through the column 300. At the same time, any liquid within the column 300 moves downward and across the succession of trays 308 in the column 300. In addition, the liquid may include a reflux stream 310 that is reinjected into the top portion of the column 300, as discussed further herein.

The column 300 may utilize a variety of separation technologies, depending on the species in the feed stream 302. For example, the column may be a distillation column, a countercurrent separation column, or a regeneration column, among others.

For a distillation column, the feed stream 302 may include a mixture of liquids with slightly different boiling points. In this case, the column 300 is a distillation column that functions to separate the species by the differences in boiling point. The trays 308 determine the number of theoretical plates, and, thus, the separation efficiency of the column 300.

In a countercurrent column, the feed stream 302 may include a mixture of gases, such as methane and $H_2O$ or $H_2S$. As the gases flow upwards through the falling stream of liquid, one gas species is preferentially absorbed by the liquid, lowering its concentration in the gas rising to the top of the column 300. In some embodiments, the liquid includes a physical solvent (not shown) that is injected into a top portion of the column 300. More specifically, the liquid and vapor phases may be counter-currently contacted to effect separation of a fluid mixture based on chemical affinities, boiling point difference, or vapor pressure differences, or combinations thereof.

In a regeneration column, the feed stream includes a liquid that contains a dissolved or adsorbed gas. As the liquid falls through the column, the gas is released, and exits through the top.

The component that concentrates in the gas phase may be flowed out of the top of the column 300 as an overhead gas stream 312, while the component that concentrates in the liquid phase may be flowed out of the bottom of the column 300 as a bottoms liquid stream 314. In addition, some amount of liquid 316 may be allowed to collect in the bottom of the column 300 before being flowed out of the column 300 in order to provide for increased separation of the gas phase from the liquid phase.

The bottoms liquid stream 314 may be flowed through a reboiler 318. The reboiler 318 may increase the temperature of the bottoms liquid stream 314, vaporizing a portion of the bottoms liquid stream 314, which may include components in the liquid, or a portion of the liquid itself. The resulting stream 320 may be flowed back into the bottom potion of the column 300 to provide heat to the liquids 316 collecting in the bottom of the column 300.

A portion of the overhead gas stream 312 may be cooled and at least partially condensed within a heat exchanger 322. The cooled gas stream 324 may then be separated into the gas stream 304 and a liquid stream 326 within a separation column 328. The liquid stream 326 may be pumped back into the top portion of the column 300 as the reflux stream 310. Within the column 300, the reflux stream 310 may be used to enhance the performance of the column 300 by increasing the degree of separation between the liquid phase and the gas phase.

In practice, the column 300 may be very large and heavy. This may create difficulty in many applications, such as offshore oil and gas production applications. Therefore, the co-current contacting system described herein may provide a desirable alternative to the column 300.

Figure 4A:
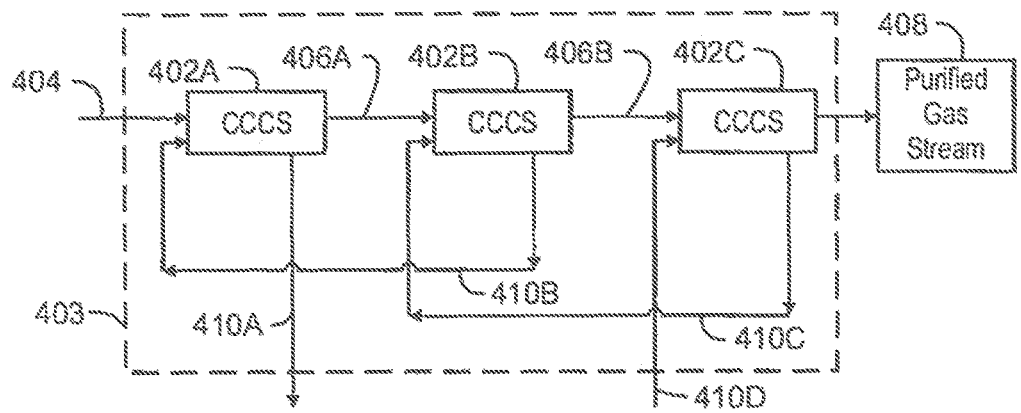
FIG. 4A is a process flow diagram of a separation system including a number of co-current contacting systems that may be placed in a shell.

FIG. 4A is a process flow diagram of a separation system 400 including a number of co-current contacting systems 402A-C that may be placed in a shell 403. In this embodiment, the separation system 400 may be analogous to a separation column, for example, as discussed with respect to FIG. 3, in which each of the co-current contacting systems 402A-C are acting as bed packing. In some embodiments, the shell 403 is a permanent, climate-controlled structure. In other embodiments, the shell 403 is a temporary or portable structure. In other embodiments, the shell 403 is an insulated jacket. The separation system 400 may be implemented as part of a gas processing system, such as the gas processing system 200 or 260 discussed with respect to FIG. 2A or 2B. The gas processing system may utilize a number of co-current contacting systems 402 connected in series, such as the co-current contacting systems 204A-F discussed with respect to FIGS. 2A and 2B. In the illustrative arrangement shown in FIG. 4A, a first co-current contacting system 402A, a second co-current contacting system 402B, and a third co-current contacting system 402C are provided, each residing within the single shell 403.

In various embodiments, due to the pump requirements on the liquid streams, the inter-stage liquid streams may be flowed through the shell 403. The shell 403 may be designed to keep the equipment and the solvent solutions flowing therein cool. This may be done through climate control within the shell 403 or through the circulation of a cooling medium adjacent to the shell 403.

A first gas stream 404 may be flowed into the first co-current contacting system 402A. The first co-current contacting system 402A may generate a first partially purified gas stream 406A, which may be flowed from the first co-current contacting system 402A to the second co-current contacting system 402B. The second co-current contacting system 402B may then generate a second partially purified gas stream 406B, which may be flowed from the second co-current contacting system 402B to the third co-current contacting system 402C. In some embodiments, the third co-current contacting system 402C generates a final purified gas stream 408.

Each of the first, second, and third co-current contacting systems 402A-402C also generates a respective rich gas treating solutions 410A, 410B, and 410C. The third gas treating solution 410C may be directed back to the second co-current contacting system 402B as a liquid solvent, and the second gas treating solution 410B may be directed back to the first co-current contacting system 402A. In addition, the third co-current contacting system 402C may receive a gas treating solution 410D from another source. Further, the first gas treating solution 410A may be returned to a regenerator (not shown), such as the regenerator 210 discussed with respect to FIGS. 2A and 2B, or may serve as a liquid solvent for a preceding co-current contacting system (not shown).

The number of co-current contacting systems is not limited to that shown. Further, the interconnections do not have to be arranged as shown. In other applications, the co-current contacting systems may be used as reactors, for example, by including a reactant in the first gas stream 404, and injecting a second reactant in the respective rich gas treating solutions 410A, 410B, and 410C.

Figure 4B:
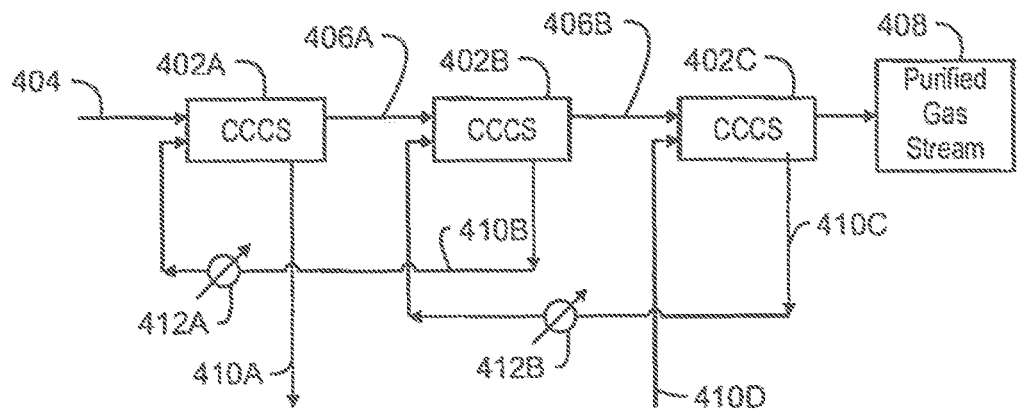
FIG. 4B is a process flow diagram of the co-current contactors of FIG. 4A with the addition of a number of heat exchangers.

FIG. 4B is a process flow diagram of the co-current contacting systems 402A, 402B, and 402C of FIG. 4A with the addition of a number of heat exchangers 412A and 412B. The heat exchangers 412A and 412B may be used to cool the gas treating solutions 410B and 410C. In some embodiments, the heat exchangers 412A and 412B are used as an alternative to the use of the shell 403.

Figure 5:
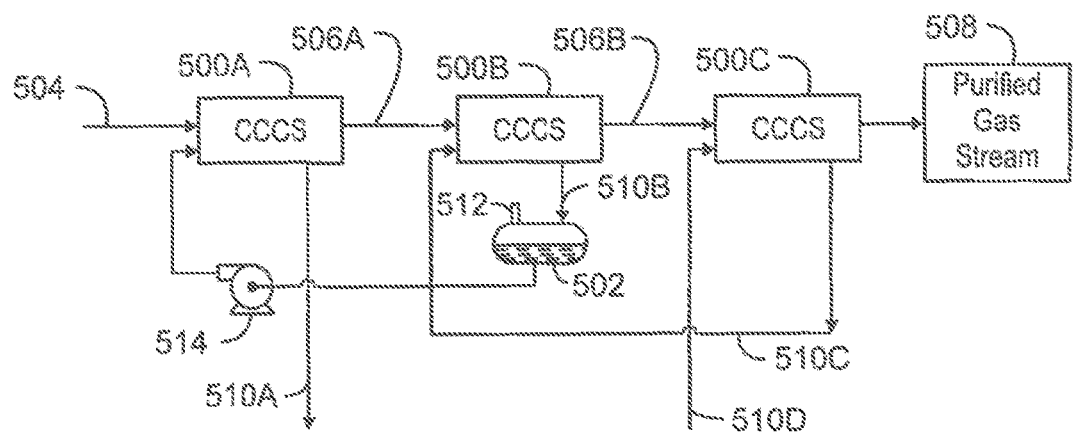
FIG. 5 is a process flow diagram of a number of co-current contactors that operate in connection with one or more flash drums.

FIG. 5 is a process flow diagram of a number of co-current contacting systems 500A-C that operate in connection with one or more flash drums 502. The co-current contacting systems 500A-C may be implemented as part of a gas processing system, such as the gas processing systems 200 or 260 discussed with respect to FIG. 2A or 2B. The co-current contacting systems 500A-C may be connected in series, similarly to the co-current contacting systems 204A-F discussed with respect to FIGS. 2A and 2B. In the illustrative arrangement shown in FIG. 5, a first co-current contacting system 500A, a second co-current contacting system 500B, and a third co-current contacting system 500C are provided.

A first gas stream 504 may be flowed into the first co-current contacting system 500A. The first co-current contacting system 500A may generate a first partially purified gas stream 506A, which may be flowed from the first co-current contacting system 500A to the second co-current contacting system 500B. The second co-current contacting system 500B may then generate a second partially purified gas stream 506B, which may be flowed from the second co-current contacting system 500B to the third co-current contacting system 500C. In some embodiments, the third co-current contacting system 500C generates a final purified gas stream 508.

Each of the first, second, and third co-current contacting systems 500A, 500B, and 500C also generates a respective rich gas treating solutions 510A, 510B, and 510C. The third gas treating solution 510C may be directed back to the second co-current contacting system 500B as a liquid solvent, and the second gas treating solution 510B may be directed back to the first co-current contacting system 500A as a liquid solvent. In addition, the third co-current contacting system 500C may receive a gas treating solution 510D from another source. Further, the first gas treating solution 510A may be returned to a regenerator (not shown), such as the regenerator 210 discussed with respect to FIGS. 2A and 2B, or may serve as a liquid solvent for a preceding co-current contacting system (not shown).

As shown in FIG. 5, the second gas treating solution 510B may be flowed through the flash drum 502. A flash line 512 may be provided coming off the top of the flash drum 502. The flash drum 502 and associated flash line 512 may permit methane and any $CO_2$ absorbed in the second gas treating solution 510B to be flashed out before the second gas treating solution 510B is flowed into the first co-current contacting system 500A. $H_2O$ in vapor form may also be vented from the flash line 512. In various embodiments, flashing the second gas treating solution 510B creates a semi-lean solvent solution. The use of a semi-lean solvent solution in the first co-current contacting system 500A may improve the efficiency of the first co-current contacting system 500A and reduce the load on the regenerator. Further, in some embodiments, any of the other gas treating solutions 510A, 510C, or 510D may also be flowed through a flash drum that is similar to the flash drum 502.

In some embodiments, gas, e.g., methane, $CO_2$, and $H_2O$, flashing out of the flash line 512 is merged with gas flashing out of flash lines associated with any number of other flash drums within the gas processing system. For example, for the gas processing system 200 discussed with respect to FIG. 2A, the gas flashing out of the flash line 512 may be merged with the natural gas 222 flashing out of the flash drum 221. The pressure of the gas flashing out of the flash line 512 may correspond to the pressure of the natural gas 222 flashing out of the flash drum 221.

As shown in FIG. 5, the second gas treating solution 510B may also be flowed through a pump 514 after it exits the flash drum 502. The pump 514 may increase the pressure of the second gas treating solution 510B, which may help to overcome the effect of the pressure drop that occurs within the co-current contacting systems 500A-C. Increasing the pressure of the second gas treating solution 510B may also allow the second gas treating solution 510B to more effectively entrain the acid gases within the gas stream 504.

The use of multiple co-current contacting systems in series has been described herein in connection with the removal of acid gases from a gas stream. For example, FIGS. 2A and 2B show applications wherein the concentration of $H_2S$ (or any other type of acid gas) within the gas stream is sequentially lowered through the use of a number of co-current contacting systems. However, the gas processing systems 200 and 260, as well any other type of gas processing system that includes a number of co-current contacting systems connected in series, may also be used for a variety of other applications.

In some embodiments, the co-current contacting systems described herein may be used for the dehydration of natural gas. Raw natural gas is often saturated with water. The water is typically removed to avoid the formation of natural gas hydrates and to prevent corrosion in pipelines.

In known operations, dehydration is commonly accomplished by contacting the wet gas stream with a glycol solvent. The glycol solvent is typically triethylene glycol (TEG). Contacting takes place in a trayed tower or a packed absorber. In operation, lean TEG, e.g., TEG that is substantially free of water, enters the top of the contactor, while the wet gas enters near the bottom of the tower. The two fluid streams flow counter-currently through the column. The downward-flowing TEG absorbs water from the upward-flowing natural gas. The natural gas exits the top of the column substantially dry, while the rich TEG exits the bottom of the column, containing the absorbed water.

One or more co-current contacting systems, such as the co-current contacting systems discussed with respect to FIGS. 2A, 2B, 4A, 4B, and 5, may be used in place of the trayed tower or packed absorber for rapidly contacting a desiccant with wet gas. In addition, higher pressure drops may be used to disperse the liquid solvent in the vapor phase and improve the efficiency of the co-current contacting systems.

Figure 6:
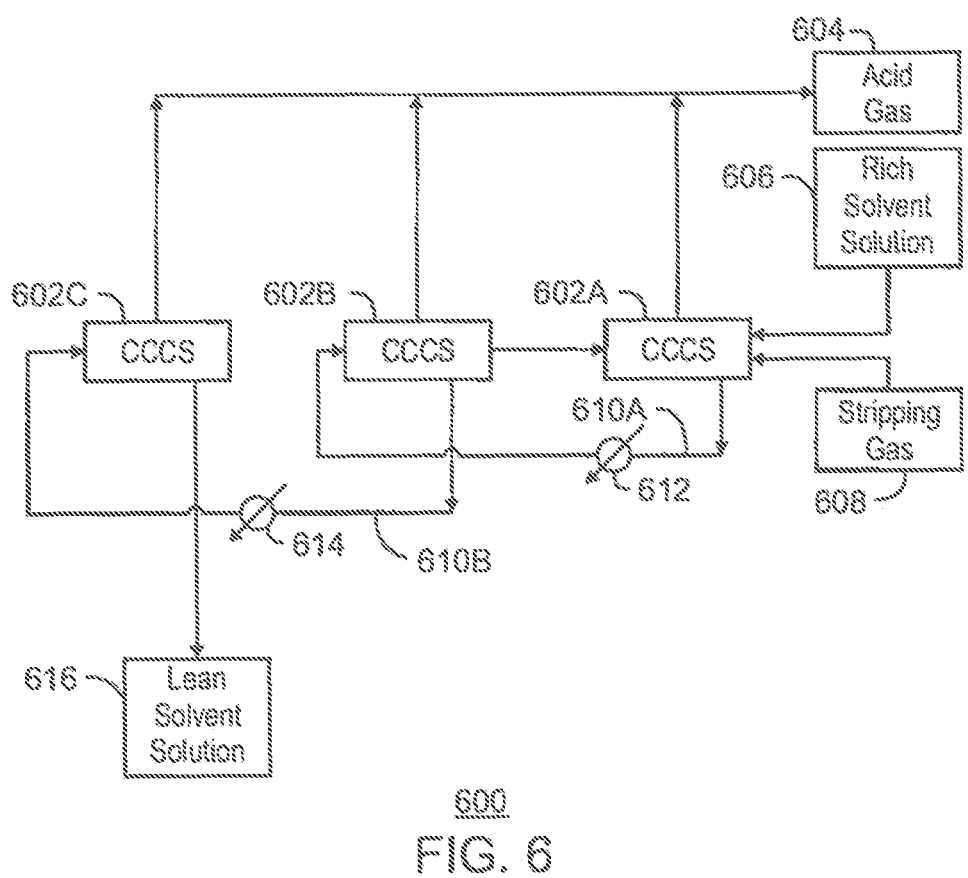
FIG. 6 is a process flow diagram of a gas regeneration facility using the co-current contacting system described herein.

FIG. 6 is a process flow diagram of a gas regeneration facility 600 using the co-current contacting system described herein. The gas regeneration facility 600 uses a series of co-current contacting systems 602A-C for the removal of acid gas 604 from a rich solvent solution 606. The rich solvent solution 606 may be warm due to the exothermic chemical reaction involved in an earlier $CO_2$ or $H_2S$ removal process, as well as possible pre-heating with an outside source.

The rich solvent solution 606 may be flowed into a first co-current contacting system 602A. Within the first co-current contacting system 602A, the rich solvent solution 606 may be contacted with a stripping gas 608. The stripping gas 608 may be nitrogen. In addition, the stripping gas 608 may be air if $H_2S$ is not present in the rich solvent solution 606, or fuel gas, such as methane, if only traces of $H_2S$ are present in the rich solvent solution 606. The stripping gas 608 may be gas generated by reboiling the liquid discharge from a third co-current contacting system 602C. Further, if $H_2S$ is present, the stripping gas 608 may be steam. If the stripping gas 608 is steam, the spent stream may be condensed, and the remaining vapor may be sent to a sulfur recovery unit, or an acid gas injection unit.

As shown in FIG. 6, a portion of the acid gas 604 within the rich solvent solution 606, which may include $CO_2$ or $H_2S$ vapor, may be flashed out of the first co-current contacting system 602A. In addition, a first partially-lean solvent solution 610A may be generated. The first partially-lean solvent solution 610A may be heated using a first heat exchanger 612. The first partially-lean solvent solution 610A may then be flowed into a second co-current contacting system 602B.

A portion of the acid gas 604 within the first partially-lean solvent solution 610A may be flashed out of the second co-current contacting system 602B. In addition, a second partially-lean solvent solution 610B may be generated. The second partially-lean solvent solution 610B may be heated using a second heat exchanger 614. The second partially-lean solvent solution 610B may then be flowed into the third co-current contacting system 602C.

The remaining acid gas 604 within the second partially-lean solvent solution 610B may be flashed out of the third co-current contacting system 602C. This may result in the generation of a lean solvent solution 616. The lean solvent solution 616 may be introduced into a co-current contacting system of a gas processing system, such as the gas processing system 200 or 260 of FIG. 2A or 2B.

In some embodiments, the rich solvent solution 606 may include water instead of acid gas. In such embodiments, the water may be removed from the rich solvent solution 606 using the co-current contacting systems 602A-C.

In various embodiments, a number of co-current contacting systems connected in series are used for the distillation of hydrocarbon mixtures or crude oil into near pure components. In such embodiments, the solvent may be steam or heated kerosene, and the gas phase may be methane and/or ethane. In addition, the hydrocarbon mixture may be heated to facilitate phase separation across the co-current contacting systems.

A number of co-current contacting systems connected in series may also be used for flash gas conditioning. In high-pressure gas purification processes, e.g. acid gas removal processes and dehydration processes, the rich solvent is often flashed into a vessel at a pressure in the range of 100 to 150 psig, for example. This flash stage releases much of the physically absorbed methane, but also releases some of the absorbed contaminants, such as $H_2S$, $CO_2$, and water vapor. To meet fuel gas specifications, this stream is often recontacted with a small slip-stream of lean solvent.

To remove impurities from the gas, a number of co-current contacting systems connected in series may be employed as absorbers. Only two or three stages may be used to remove the impurities, as the $H_2S$ specification for flash gas is generally not as stringent as that for pipeline gas. The flash gas may be used as fuel gas within a gas processing system, such as the gas processing system 200 or 260 of FIG. 2A or 2B, instead of being sold commercially.

In some embodiments, the gas stream represents gas from a catalytic hydro-desulfurization process (CHDS). In oil refineries, CHDS is sometimes used to convert mercaptans, sulfides, thiophenes, and other sulfur-containing compounds to $H_2S$. As an incidental byproduct of the CHDS, light hydrocarbons may be produced. It is possible to treat this gas to remove the $H_2S$, and then use the treated gas as fuel, for example. Such treatment may be accomplished using a series of co-current contacting systems, such as the co-current contacting systems discussed with respect to FIGS. 2A, 2B, 4A, 4B, 5, and 6.

A number of techniques have been demonstrated herein for sequentially removing acid gases from a raw gas stream by using two or more co-current contacting systems connected in series. Some of the techniques described herein involve the removal of acid gases, either partially or completely, and either selectively or non-selectively, from hydrocarbon gas streams. The gas stream may be a natural gas stream, a combustion exhaust gas stream, or a refining gas stream, for example. The absorbent liquid may include an absorption solution including at least one chemical compound such as monoethanolamine (MEA), diglycolamine (DGA), diethanolamine (DEA), methyldiethanolamine (MDEA), 2-amino-2-methyl-1-propanol (AMP), piperazine (PZ), ammonia, amines, alkanolamines, their derivatives, and other chemical solvents and/or mixtures thereof. The absorbent liquid may also include at least one chemical component such as kinetic enhancers, corrosion inhibitors, anti-foam chemicals, oxygen scavengers, salts, neutralizers, anti-fouling chemicals, and anti-degradation chemicals.

The absorbent liquid may include at least one chemical component selected for absorbing, assimilating, or otherwise reacting with a gas, such as $CO_2$, $H_2S$, $SO_2$, and $NO_R$. Alternatively, the absorbent liquid may include a desiccating liquid including at least one chemical compound such as monoethylene glycol (MEG), diethylene glycol (DEG), or triethylene glycol (TEG). In this example, the gaseous component selected for removal in this case is $H_2O$.

Co-Current Contacting System

Figure 7:
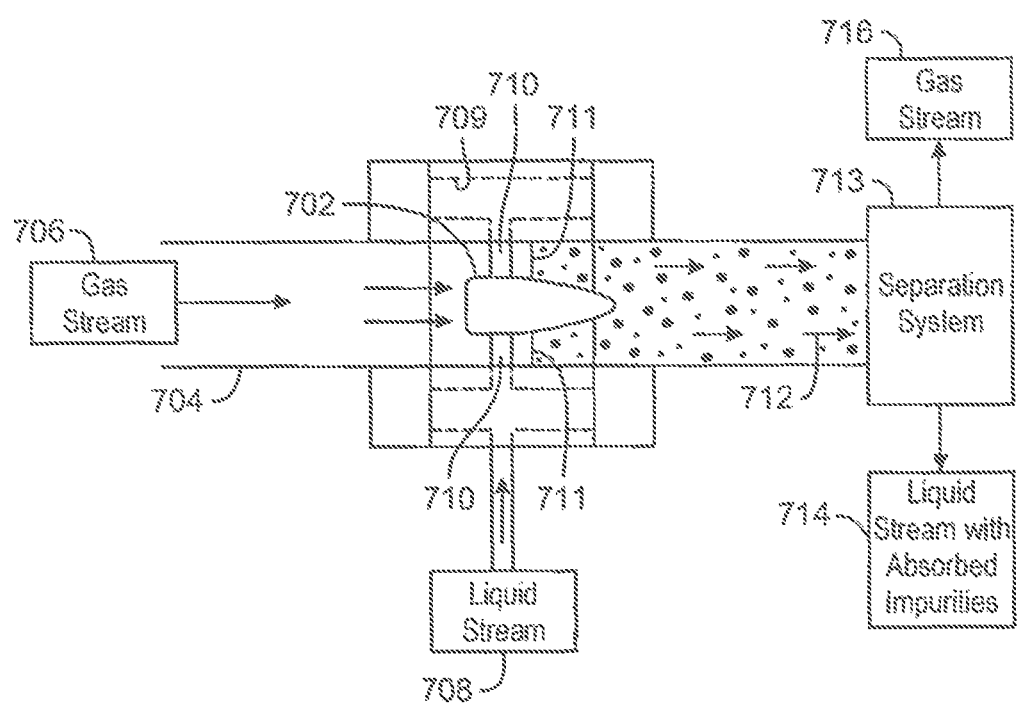
FIG. 7 is a schematic of a co-current contacting system.

FIG. 7 is a schematic of a co-current contacting system 700. The co-current contacting system 700 may provide for the separation of components within a gas stream. In addition, the co-current contacting system 700 may aid in the implementation of various gas processing systems, such as the gas processing systems 200 and 260 of FIGS. 2A and 2B, where the rapid separation of components is desired. In some embodiments, the co-current contacting system 700 is one of the co-current contacting systems 204A-F, 402A-C, 500A-C, and 602A-C discussed with respect to FIGS. 2A, 2B, 4A, 4B, 5, and 6.

The co-current contacting system 700 may include a co-current contactor 702 that is positioned in-line within a pipe 704. The co-current contactor 702 may include a number of components that provide for the efficient contacting of a liquid droplet stream with a flowing gas stream 706. The liquid droplet stream can be used for the separation of impurities, such as $H_2O$, $H_2S$, or $CO_2$, from a gas stream 706.

As shown in FIG. 7, the gas stream 706 may be flowed through the pipe 704 and into the co-current contactor 702. A liquid stream 708 may also be flowed into the co-current contactor 702, for example, into a hollow space 709 coupled to flow channels 710 in the co-current contactor 702. The liquid stream 708 may include any type of treating liquid that is capable of removing the impurities from the gas stream 706.

From the flow channels 710, the liquid stream 708 is released into the gas stream 706 as fine droplets through injection orifices 711, resulting in a treated gas stream 712. This may result in the generation of a treated gas stream 712. The treated gas stream 712 may include small liquid droplets dispersed in a gas phase. The liquid droplets may include impurities from the gas stream 706 that were adsorbed or dissolved into the liquid stream 708.

The treated gas stream 712 may be flowed into a separation system 713, such as a cyclonic separator, a mesh screen, or a settling vessel. The separation system 713 removes the liquid droplets from the gas phase. The liquid droplets may include the original liquid stream with the incorporated impurities 714, and the gas phase may include a purified gas stream 716. In some embodiments, the purified gas stream 716 is a dehydrated gas stream that has been purified via the removal of $H_2O$. In other embodiments, the purified gas stream 716 is a purified gas stream that has been purified via the removal of $H_2S$ or $CO_2$, for example.

Figure 8A:
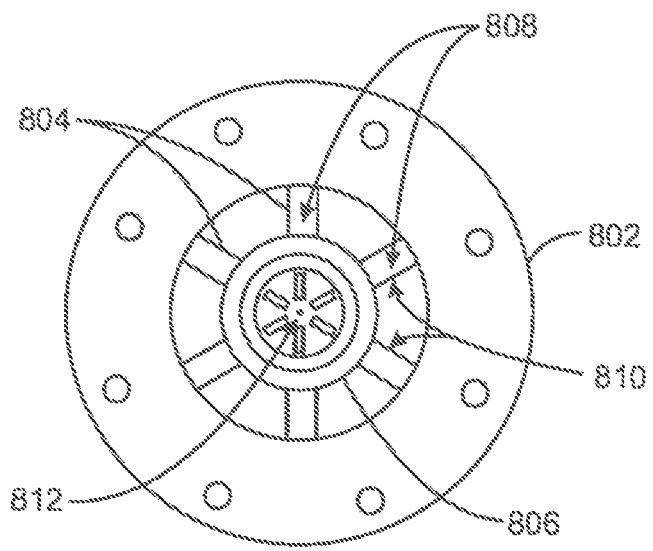
FIG. 8A is a front view of a co-current contactor.

FIG. 8A is a front view of a co-current contactor 800. The co-current contactor 800 may be implemented within a co-current contacting system, such as the co-current contacting system 700 discussed with respect to FIG. 7. The co-current contactor 800 may be an axial, in-line co-current contactor located within a pipe. The front view of the co-current contactor 800 represents an upstream view of the co-current contactor 800.

The co-current contactor 800 may include an outer annular support ring 802, a number of radial blades 804 extending from the annular support ring 802, and a central gas entry cone 806. The annular support ring 802 may secure the co-current contactor 800 in-line within the pipe. In addition, the radial blades 804 may provide support for the central gas entry cone 806.

The annular support ring 802 may be designed as a flanged connection, or as a removable or fixed sleeve inside the pipe. In addition, the annular support ring 802 may include a liquid feed system and a hollow channel discussed further with respect to FIGS. 7, 8C and 8D. A liquid stream may be fed to the co-current contactor 800 via the hollow channel in the annular support ring 802. The hollow channel may allow equal distribution of the liquid stream along the perimeter of the co-current contactor 800.

Small liquid channels within the annular support ring 802 may provide a flow path for the liquid stream to flow through injection orifices 808 within the radial blades 804. The liquid injection orifices 808 may be located on or near the leading edge of each radial blade 804. Placement of the liquid injection orifices 808 on the radial blades 804 may allow the liquid stream to be uniformly distributed in a gas stream that is directed between the radial blades 804. Specifically, the liquid stream may be contacted by the gas stream flowing through the gaps between the radial blades 804, and may be sheared into small droplets and entrained in the gas phase.

The gas stream may also be flowed into the central gas entry cone 806 through a gas inlet 812. The central gas entry cone 806 may block a cross-sectional portion of the pipe. The radial blades 804 include gas exit slots 810 that allow the gas stream to be flowed out of the central gas entry cone 806. This may increase the velocity of the gas stream as it flows through the pipe. The central gas entry cone 806 may direct a predetermined amount of the gas stream to the gas exit slots 810 on the radial blades 804.

Some of the liquid stream injected through the radial blades 804 may be deposited on the surface of the radial blades 804 as a liquid film. As the gas stream flows through the central gas entry cone 806 and is directed out of the gas exit slots 810 on the radial blades 804, the gas stream may sweep, or blow, much of the liquid film off the radial blades 804. This may enhance the dispersion of the liquid stream into the gas phase. Further, the obstruction to the flow of the gas stream and the shear edges created by the central gas entry cone 806 may provide a zone with an increased turbulent dissipation rate. The may result in the generation of smaller droplets that enhance the mass transfer rate of the liquid stream and the gas stream.

The size of the co-current contactor 800 may be adjusted such that the gas stream flows at a high velocity. This may be accomplished via either a sudden reduction in the diameter of the annular support ring 802 or a gradual reduction in the diameter of the annular support ring 802. The outer wall of the co-current contactor 800 may be slightly converging in shape, terminating at the point where the gas stream and the liquid stream are discharged into the downstream pipe. This may allow for the shearing and re-entrainment of any liquid film that is removed from the co-current contactor 800. Further, a radial inward ring, grooved surface, or other suitable equipment may be included on the outer diameter of the co-current contactor 800 near the point where the gas stream and the liquid stream are discharged into the downstream pipe. This may enhance the degree of liquid entrainment within the gas phase.

The downstream end of the co-current contactor 800 may discharge into a section of pipe (not shown). The section of pipe may be a straight section of pipe, or a concentric expansion section of pipe. In some embodiments, the central gas entry cone 806 terminates with a blunt ended cone or a tapered ended cone. In other embodiments, the central gas entry cone 806 terminates with a ridged cone, which may include multiple concentric ridges along the cone that provide multiple locations for droplet generation. In addition, any number of gas exit slots 810 may be provided on the cone itself to allow for the removal of the liquid film from the co-current contactor 800.

Figure 8B:
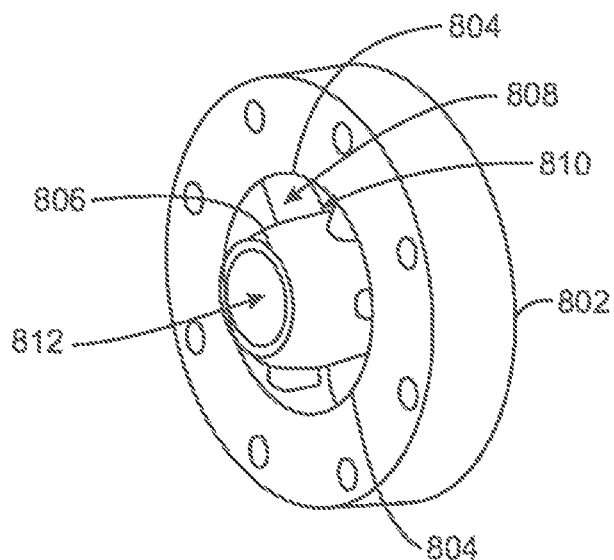
FIG. 8B is a side perspective view of the co-current contactor.

FIG. 8B is a side perspective view of the co-current contactor 800. Like numbered items are as described with respect to FIG. 8A. As shown in FIG. 8B, the upstream portion of the central gas entry cone 806 may extend further into the pipe than the annular support ring 802 and the radial blades 804 in the upstream direction. The downstream portion of the central gas entry cone 806 may also extend further into the pipe than the annular support ring 802 and the radial blades 804 in the downstream direction. The length of the central gas entry cone 806 in the downstream direction depends on the type of cone at the end of the central gas entry cone 806, as discussed further with respect to FIGS. 8C and 8D.

Figure 8C:
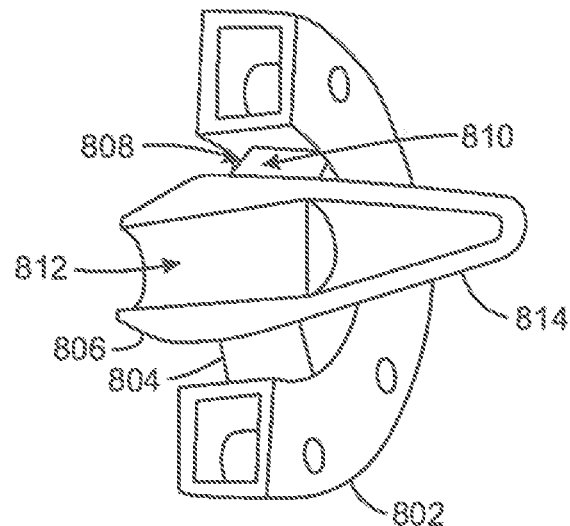
FIG. 8C is a cross-sectional side perspective view of the co-current contactor.

FIG. 8C is a cross-sectional side perspective view of the co-current contactor 800. Like numbered items are as described with respect to FIGS. 8A and 8B. According to the embodiment shown in FIG. 8C, the central gas entry cone 806 of the co-current contactor 800 terminates with a tapered ended cone 814. Terminating the central gas entry cone 806 with a tapered ended cone 814 may reduce the overall pressure drop in the pipe caused by the co-current contactor 800.

Figure 8D:
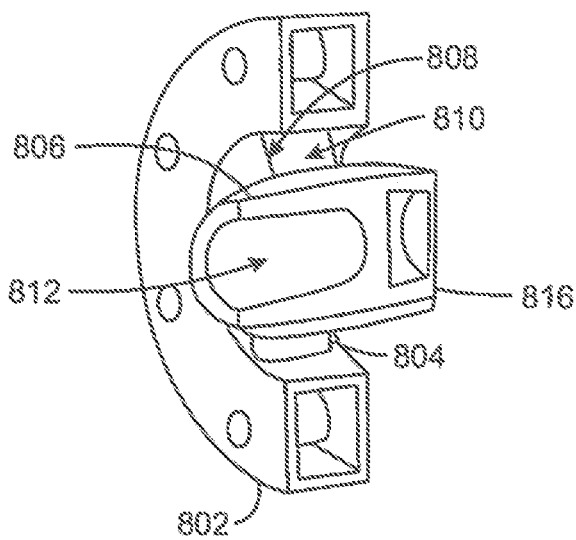
FIG. 8D is a another cross-sectional side perspective view of the co-current contactor.

FIG. 8D is another cross-sectional side perspective view of the co-current contactor 800. Like numbered items are as described with respect to FIGS. 8A-C. According to the embodiment shown in FIG. 8D, the central gas entry cone 806 of the co-current contactor 800 terminates with a blunt ended cone 816. Terminating the central gas entry cone 806 with a blunt ended cone 816 may encourage droplet formation in the center of the pipe.

Method for Contacting a Gas Stream with a Liquid Stream

Figure 9:
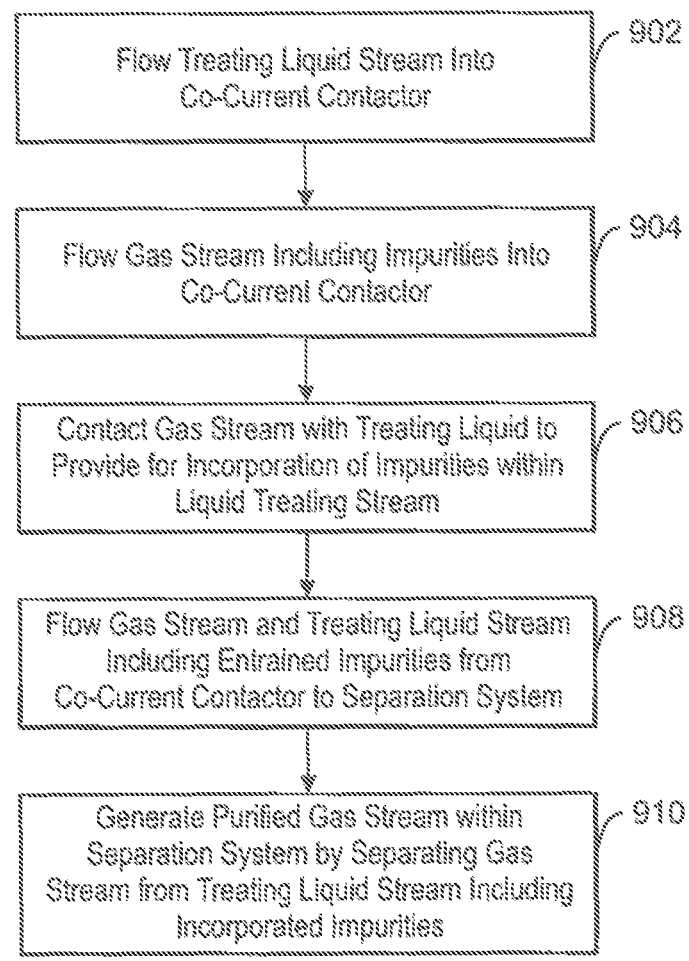
FIG. 9 is a process flow diagram showing a method for contacting a gas stream with a liquid stream.

FIG. 9 is a process flow diagram showing a method 900 for contacting a gas stream with a liquid stream. The method 900 may be implemented by one or more co-current contacting systems, such as any of the co-current contacting systems 204A-F, 402A-C, 500A-C, 602A-C, and 700 discussed with respect to FIG. 2A, 2B, 4A, 4B, 5, 6, or 7. Further, the method 900 may be implemented within a gas processing system, such as the gas processing system 200 or 260 discussed with respect to FIG. 2A or 2B.

The method begins at block 902, at which a liquid stream is flowed into a co-current contactor. The liquid stream may be flowed into the co-current contactor via an annular support ring and a number of radial blades extending from the annular support ring. The annular support ring may secure the co-current contactor in-line within a pipe. The liquid stream may be any suitable type of absorbent liquid stream, for example.

At block 904, a gas stream is flowed into the co-current contactor. The gas stream may be flowed into the co-current contactor via a central gas entry cone that is supported by the radial blades. The gas stream may be a natural gas stream, for example.

At block 906, the gas stream is contacted with the liquid stream within the co-current contactor to provide for incorporation of liquid droplets formed from the liquid stream into the gas stream. In various embodiments, impurities within the gas stream are incorporated into the liquid droplets. Such impurities may include water or acid gas, such as $H_2S$ or $CO_2$, for example.

In some embodiments, the central gas entry cone increases the turbulence of the gas flow by partially obstructing the gas flow. Such an increase in turbulence may result in an increase in the amount of dispersion of the liquid droplets within the gas stream. In addition, shearing forces created by the shape of the co-current contactor may aid in the dispersion of the liquid droplets within the gas stream.

At block 908, the liquid droplets are separated from the gas stream within a separation system. The separation system may be a cyclonic separator or a separation column, for example. In various embodiments, impurities that have been incorporated into the liquid droplets are also separated from the gas stream along with the liquid droplets. This may result in the generation of a purified gas stream (block 910). For example, if the gas stream is a natural gas stream, and the impurities include water, the natural gas stream may be dehydrated via the removal of the water. As another example, if the gas stream is a natural gas stream, and the impurities include acid gas, the natural gas stream may be sweetened via the removal of the acid gas.

The process flow diagram of FIG. 9 is not intended to indicate that the steps of the method 900 are to be executed in any particular order, or that all of the steps of the method 900 are to be included in every cases. Further, any number of additional steps not shown in FIG. 9 may be included within the method 900, depending on the details of the specific implementation. For example, the gas stream may be flowed through any number of additional co-current contactors and separations systems connected in series within the pipe. In some embodiments, the co-current contactors and separation systems progressively purify the gas stream by removing residual impurities. Further, in some embodiments, the impurities are removed from the liquid stream downstream of the separation system. The liquid stream may then be recycled to the co-current contactor, or may be flowed into another co-current contactor.

Furthermore, the method 900 may be used for quench applications. For example, the method 900 may be used for injection of cooling water or direct injection of hot oil for ethylene quenching applications. In addition, the method 900 may be used for water wash applications, such as water wash applications including an acid gas absorber overhead stream.

Embodiments

Embodiments of the invention may include any combinations of the methods and systems shown in the following numbered paragraphs. This is not to be considered a complete listing of all possible embodiments, as any number of variations can be envisioned from the description above.

1. A co-current contacting system, including:
a co-current contactor located in-line within a pipe, the co-current contactor including:
an annular support ring configured to maintain the co-current contactor within the pipe;
a number of radial blades configured to allow a liquid stream to flow into the co-current contactor; and
a central gas entry cone configured to allow a gas stream to flow through a hollow section within the co-current contactor;
wherein the co-current contactor provides for efficient incorporation of liquid droplets formed from the liquid stream into the gas stream; and
a separation system configured to remove at least a portion of the liquid droplets from the gas stream.
2. The co-current contacting system of paragraph 1, wherein the gas stream includes impurities that are incorporated into the liquid droplets within the co-current contactor.
3. The co-current contacting system of paragraph 2, wherein the separation system generates a purified gas stream by removing at least a portion of the liquid droplets including the impurities from the gas stream.
4. The co-current contacting system of any of paragraphs 2 or 3, wherein the gas stream includes a natural gas stream, and wherein the impurities include water.
5. The co-current contacting system of any of paragraphs 2-4, wherein the gas stream includes a natural gas stream, and wherein the impurities include an acid gas.
6. The co-current contacting system of any of paragraphs 1 or 2, wherein the separation system includes a cyclonic separator.
7. The co-current contacting system of any of paragraphs 1, 2, or 6, wherein the separation system includes a distillation column.
8. The co-current contacting system of any of paragraphs 1, 2, 6, or 7, wherein a downstream portion of the central gas entry cone includes a blunt ended cone.
9. The co-current contacting system of any of paragraphs 1, 2, or 6-8, wherein a downstream portion of the central gas entry cone includes a tapered ended cone.
10. The co-current contacting system of any of paragraphs 1, 2, or 6-9, wherein the liquid stream includes an absorbent liquid stream.
11. The co-current contacting system of any of paragraphs 1, 2, or 6-10, including a number of co-current contacting systems connected in series within the pipe.
12. The co-current contacting system of any of paragraphs 1, 2, or 6-11, wherein the co-current contacting system is implemented within a gas processing system.
13. The co-current contacting system of any of paragraphs 1, 2, or 6-12, wherein the co-current contacting system is used for quench applications.
14. The co-current contacting system of any of paragraphs 1, 2, or 6-13, wherein the co-current contacting system is used for water wash applications.
15. A method for separating impurities from a gas stream, including:
flowing a liquid stream into a co-current contactor via an annular support ring and a number of radial blades extending from the annular support ring, wherein the annular support ring secures the co-current contactor in-line within a pipe;
flowing a gas stream into the co-current contactor via a central gas entry cone that is supported by the number of radial blades, wherein a first portion of the gas stream flows through the central gas entry cone and a second portion of the gas stream flows around the central gas entry cone between the number of radial blades;
contacting the gas stream with the liquid stream to provide for incorporation of liquid droplets formed from the liquid stream into the gas stream; and
separating the liquid droplets from the gas stream within a separation system.
16. The method of paragraph 15, including flowing the gas stream through a number of co-current contactors and separation systems connected in series within the pipe.
17. The method of any of paragraphs 15 or 16, including incorporating impurities from the gas stream into the liquid droplets within the co-current contactor.
18. The method of paragraph 17, including generating a purified gas stream by removing at least a portion of the liquid droplets including the impurities from the gas stream within the separation system.
19. The method of any of paragraphs 17 or 18, wherein the gas stream includes a natural gas stream, and wherein the impurities include water.
20. The method of paragraph 19, including generating a dehydrated natural gas stream by removing liquid droplets including incorporated water from the natural gas stream.
21. The method of any of paragraphs 17-19, wherein the gas stream includes a natural gas stream, and wherein the impurities include acid gas.
22. The method of paragraph 21, including generating a sweetened natural gas stream by removing liquid droplets including incorporated acid gas from the natural gas stream.
23. The method of any of paragraphs 21 or 22, wherein the acid gas includes hydrogen sulfide or carbon dioxide, or any combination thereof 24. A co-current contactor, including:

an annular support ring configured to maintain the co-current contactor in-line within a pipe, wherein the annular support ring includes a hollow channel configured to allow a liquid stream to flow into a number of radial blades extending from the annular support ring; and a central gas entry cone configured to allow a gas stream to flow into the co-current contactor, wherein a first portion of the gas stream flows through the central gas entry cone and a second portion of the gas stream flows around the central gas entry cone between the number of radial blades;

wherein the co-current contactor is configured to provide for incorporation of liquid droplets formed from the liquid stream into the gas stream.

25. The co-current contactor of paragraph 24, wherein each radial blade includes a number of liquid injection orifices configured to allow the liquid stream to flow into the radial blade.

26. The co-current contactor of any of paragraphs 24 or 25, wherein the central gas entry cone increases a velocity of the gas stream as the gas stream flows into the co-current contactor.

27. The co-current contactor of any of paragraphs 24-26, wherein the central gas entry cone includes a central obstruction to gas flow that results in an increased turbulence, and wherein the increased turbulence increases an amount of dispersion of the liquid droplets within the gas stream.

28. The co-current contactor of any of paragraphs 24-27, wherein the central gas entry cone terminates with a blunt ended cone.

29. The co-current contactor of any of paragraphs 24-28, wherein the central gas entry cone terminates with a tapered ended cone.

30. The co-current contactor of any of paragraphs 24-29, wherein impurities from the gas stream are incorporated into the liquid droplets.

31. The co-current contactor of paragraph 30, wherein the impurities include water.

32. The co-current contactor of any of paragraphs 30 or 31, wherein the impurities include acid gas.

33. The co-current contactor of any of paragraphs 24-30, wherein the gas stream includes a natural gas stream.

While the present techniques may be susceptible to various modifications and alternative forms, the embodiments discussed above have been shown only by way of example. However, it should again be understood that the techniques is not intended to be limited to the particular embodiments disclosed herein. Indeed, the present techniques include all alternatives, modifications, and equivalents falling within the true spirit and scope of the appended claims.

What is claimed is:

1. A co-current contacting system, comprising:

a co-current contactor located in-line within a pipe, the co-current contactor comprising:

an annular support ring configured to maintain the co-current contactor in-line within the pipe;

a plurality of radial blades extending from the annular support ring;

gas exit slots included in the plurality of radial blades;

injection orifices disposed on the plurality of radial blades;

wherein the annular support ring comprises a hollow channel configured to allow a liquid stream to flow into the plurality of radial blades and out of the injection orifices, the injection orifices configured to inject the liquid stream into a gas stream flowing into the co-current contactor; and a central gas entry cone that is supported by the plurality of radial blades and having a hollow section, the central gas entry cone configured to allow the gas stream to flow into the co-current contactor, wherein a first portion of the gas stream flows through the hollow section of the central gas entry cone and through the gas exit slots, and wherein a second portion of the gas stream flows around the central gas entry cone and between the plurality of radial blades;

wherein the co-current contactor provides for efficient incorporation of liquid droplets formed from the liquid stream exiting the injection orifices into the gas stream; and a separation system configured to remove at least a portion of the liquid droplets from the gas stream.

2. The co-current contacting system of claim 1, wherein the gas stream comprises impurities that are incorporated into the liquid droplets within the co-current contactor.

3. The co-current contacting system of claim 2, wherein the separation system generates a purified gas stream by removing at least a portion of the liquid droplets comprising the impurities from the gas stream.

4. The co-current contacting system of claim 2, wherein the gas stream comprises a natural gas stream, and wherein the impurities comprise water.

5. The co-current contacting system of claim 2, wherein the gas stream comprises a natural gas stream, and wherein the impurities comprise an acid gas.

6. The co-current contacting system of claim 1, wherein the separation system comprises a cyclonic separator.

7. The co-current contacting system of claim 1, wherein the separation system comprises a distillation column.

8. The co-current contacting system of claim 1, wherein a downstream portion of the central gas entry cone comprises a blunt ended cone.

9. The co-current contacting system of claim 1, wherein a downstream portion of the central gas entry cone comprises a tapered ended cone.

10. The co-current contacting system of claim 1, wherein the liquid stream comprises an absorbent liquid stream.

11. The co-current contacting system of claim 1, comprising a plurality of co-current contacting systems connected in series within the pipe.

12. The co-current contacting system of claim 1, wherein the co-current contacting system is implemented within a gas processing system.

13. The co-current contacting system of claim 1, wherein the co-current contacting system is used for quench applications.

14. The co-current contacting system of claim 1, wherein the co-current contacting system is used for water wash applications.

15. A method for separating impurities from a gas stream, comprising:

flowing a liquid stream into a co-current contactor via a hollow channel in an annular support ring and a plurality of radial blades extending from the annular support ring, wherein the annular support ring secures the co-current contactor in-line within a pipe and wherein injection orifices are disposed on the plurality of radial blades;

injecting the liquid stream into a gas stream flowing into the co-current contactor via the injection orifices;

flowing the gas stream into the co-current contactor via a central gas entry cone that is supported by the plurality of radial blades, wherein a first portion of the gas stream flows through the central gas entry cone, and wherein a second portion of the gas stream flows around the central gas entry cone and between the plurality of radial blades;

flowing the first portion of the gas stream through a hollow section in the central gas entry cone and through gas exit slots included in the plurality of radial blades;

contacting the gas stream with the liquid stream to provide for incorporation of liquid droplets formed from the liquid stream exiting the injection orifices into the gas stream; and separating the liquid droplets from the gas stream within a separation system.

16. The method of claim 15, comprising flowing the gas stream through a plurality of co-current contactors and separation systems connected in series within the pipe.

17. The method of claim 15, comprising incorporating impurities from the gas stream into the liquid droplets within the co-current contactor.

18. The method of claim 17, comprising generating a purified gas stream by removing at least a portion of the liquid droplets comprising the impurities from the gas stream within the separation system.

19. The method of claim 17, wherein the gas stream comprises a natural gas stream, and wherein the impurities comprise water.

20. The method of claim 19, comprising generating a dehydrated natural gas stream by removing liquid droplets comprising incorporated water from the natural gas stream.

21. The method of claim 17, wherein the gas stream comprises a natural gas stream, and wherein the impurities comprise acid gas.

22. The method of claim 21, comprising generating a sweetened natural gas stream by removing liquid droplets comprising incorporated acid gas from the natural gas stream.

23. The method of claim 21, wherein the acid gas comprises hydrogen sulfide or carbon dioxide, or any combination thereof.

24. A co-current contactor, comprising:

an annular support ring configured to maintain the co-current contactor in-line within a pipe;

a plurality of radial blades extending from the annular support ring;

gas exit slots included in the plurality of radial blades;

injection orifices disposed on the plurality of radial blades;

wherein the annular support ring comprises a hollow channel configured to allow a liquid stream to flow into the plurality of radial blades and out of the injection orifices, the injection orifices configured to inject the liquid stream into a gas stream flowing into the co-current contactor;

a central gas entry cone that is supported by the plurality of radial blades and having a hollow section, the central gas entry cone configured to allow the gas stream to flow into the co-current contactor, wherein a first portion of the gas stream flows through the hollow section of the central gas entry cone and through the gas exit slots, and wherein a second portion of the gas stream flows around the central gas entry cone and between the plurality of radial blades;

wherein the co-current contactor is configured to provide for incorporation of liquid droplets formed from the liquid stream exiting the injection orifices into the gas stream.

25. The co-current contactor of claim 24, wherein the central gas entry cone terminates with at least one of a blunt ended cone and a tapered ended cone.

26. The co-current contactor of claim 24, wherein the central gas entry cone comprises a central obstruction to gas flow that results in an increased turbulence, and wherein the increased turbulence increases an amount of dispersion of the liquid droplets within the gas stream.

27. The co-current contactor of claim 24, wherein impurities from the gas stream are incorporated into the liquid droplets, and the impurities comprise one or more of water, acid gas and a natural gas stream.

* * * * *